United States Patent
McCreery

(10) Patent No.: US 12,144,763 B2
(45) Date of Patent: Nov. 19, 2024

(54) METHODS AND DEVICES FOR TREATING SLEEP APNEA

(71) Applicant: Huntington Medical Research Institutes, Pasadena, CA (US)

(72) Inventor: Douglas B. McCreery, Pasadena, CA (US)

(73) Assignee: Huntington Medical Research Institutes, Pasadena, CA (US)

( * ) Notice: Subject to any disclaimer, the term of this patent is extended or adjusted under 35 U.S.C. 154(b) by 0 days.

(21) Appl. No.: 18/301,922

(22) Filed: Apr. 17, 2023

(65) Prior Publication Data

US 2023/0381009 A1   Nov. 30, 2023

Related U.S. Application Data

(63) Continuation of application No. 16/164,539, filed on Oct. 18, 2018, now Pat. No. 11,654,045.

(51) Int. Cl.
*A61F 5/56* (2006.01)
*A61B 5/00* (2006.01)
(Continued)

(52) U.S. Cl.
CPC ............ *A61F 5/566* (2013.01); *A61B 5/486* (2013.01); *A61B 5/682* (2013.01); *A61N 1/0548* (2013.01);
(Continued)

(58) Field of Classification Search
CPC ............ A61B 5/682; A61B 2562/0238; A61B 5/0088; A61B 5/0261; A61B 5/1107;
(Continued)

(56) References Cited

U.S. PATENT DOCUMENTS

| 4,593,686 A | 6/1986 | Lloyd et al. |
| 5,284,161 A * | 2/1994 | Karell ............... A61F 5/566 600/382 |

(Continued)

FOREIGN PATENT DOCUMENTS

| CA | 2738479 A1 | 4/2010 |
| CN | 206391069 U | 8/2017 |

(Continued)

OTHER PUBLICATIONS

Extended European Search Report dated Sep. 23, 2009, received in European Application 07843352.1 filed Sep. 27, 2007, 9 pages.
(Continued)

*Primary Examiner* — Amanda K Hulbert
(74) *Attorney, Agent, or Firm* — KPPB LLP

(57) ABSTRACT

An intraoral stimulation device configured to be positioned in a mouth of a patient. The device includes a sensor and one or more electrodes. The sensor is configured to monitor a position of the tongue and/or force exerted by the tongue against the sensor and to transmit a signal encoding tongue information. The electrode(s) is/are configured to deliver electrical stimuli to the patient's hard palate when the tongue information indicates that the tongue has moved from a desired position to an undesired position in the mouth. The electrical stimuli causes the tongue to move from the undesired position to the desired position.

24 Claims, 11 Drawing Sheets

(51) Int. Cl.
*A61N 1/05* (2006.01)
*A61N 1/36* (2006.01)
(52) U.S. Cl.
CPC ..... *A61N 1/36031* (2017.08); *A61N 1/36078* (2013.01); *A61N 1/3611* (2013.01); *A61B 5/4818* (2013.01)
(58) Field of Classification Search
CPC ... A61B 5/4552; A61B 5/4818; A61B 5/4836; A61B 5/486; A61C 1/088; A61F 2005/563; A61F 5/566; A61N 1/0548; A61N 1/3601; A61N 1/36031; A61N 1/3611; A61N 1/36078
See application file for complete search history.

(56) References Cited

U.S. PATENT DOCUMENTS

| | | |
|---|---|---|
| 5,792,067 A | 8/1998 | Karell |
| 6,598,006 B1 | 7/2003 | Honda et al. |
| 7,711,438 B2 | 5/2010 | Lattner et al. |
| 7,890,193 B2 | 2/2011 | Tingey |
| 8,249,723 B2 | 8/2012 | Mccreery |
| 8,359,108 B2 | 1/2013 | Mccreery |
| 8,774,943 B2 | 7/2014 | Mccreery |
| 11,654,045 B2 | 5/2023 | McCreery |
| 2003/0025082 A1 | 2/2003 | Brewington et al. |
| 2005/0045190 A1 | 3/2005 | Bennett |
| 2007/0173893 A1 | 7/2007 | Pitts |
| 2009/0048647 A1 | 2/2009 | Tingey |
| 2010/0087896 A1 | 4/2010 | McCreery |
| 2010/0185254 A1 | 7/2010 | Lindquist et al. |
| 2010/0204747 A1 | 8/2010 | Lindquist et al. |
| 2012/0234331 A1 | 9/2012 | Shantha |
| 2012/0234332 A1 | 9/2012 | Shantha |
| 2012/0239111 A1 | 9/2012 | Mccreery |
| 2013/0085546 A1 | 4/2013 | Bolea et al. |
| 2013/0190836 A1* | 7/2013 | McCreery ............ A61B 5/4552 607/42 |
| 2014/0323839 A1 | 10/2014 | Mccreery |
| 2015/0190630 A1 | 7/2015 | Kent et al. |
| 2017/0087360 A1 | 3/2017 | Scheiner |
| 2017/0143259 A1 | 5/2017 | Kent et al. |
| 2017/0290699 A1 | 10/2017 | Radmand |
| 2020/0121492 A1 | 4/2020 | McCreery |

FOREIGN PATENT DOCUMENTS

| | | |
|---|---|---|
| CN | 113423366 A | 9/2021 |
| EP | 3866736 A1 | 8/2021 |
| IN | 524174 | 3/2024 |
| KR | 20130029184 A | 3/2013 |
| KR | 20140134160 A | 11/2014 |
| TW | 200501437 A | 1/2005 |
| WO | 1992015364 A1 | 9/1992 |
| WO | 1997018854 A1 | 5/1997 |
| WO | 1997018857 A1 | 5/1997 |
| WO | 2008039921 A2 | 4/2008 |
| WO | 2008039921 A3 | 6/2008 |
| WO | 2020081831 A1 | 4/2020 |

OTHER PUBLICATIONS

Extended European Search Report for European Application No. 19874579.6, Search completed May 27, 2022, Mailed Jun. 7, 2022, 09 Pgs.

International Preliminary Report on Patentability for International Application PCT/US2007/079717, Report issued Mar. 31, 2009, Mailed Mar. 31, 2009, 8 Pgs.

International Preliminary Report on Patentability for International Application PCT/US2019/056763, Report issued Apr. 14, 2021, Mailed Apr. 29, 2021 11 Pgs.

International Search Report and Written Opinion for International Application No. PCT/US2019/056763, Search completed Dec. 13, 2019, Mailed Jan. 8, 2020, 18 Pgs.

International Search Report and Written Opinion for International Application No. PCT/US2007/079717, Search completed Mar. 18, 2008, Mailed Apr. 18, 2008, 8 Pgs.

Fletcher et al., "Glossometric measurements in vowel production and modification", Clinical Linguistics & Phonetics, 1989, vol. 3, No. 4, 359-375.

Wrench et al., "Optopalatograph (OPG): A new apparatus for speech production analysis", Proc. Intl. Conf. Spoken Language Processing, 1996; pp. 1589-1592.

English Abstract of TW 200501437, obtained from http://twpat6.tipo.gov.tw/tipotwoc/, Published Jan. 1, 2005, 1 pg.

Chwiesko-Minarowska et al., "Rehabilitation of Patients with Obstructive Sleep Apnea Syndrome", International Journal of Rehabilitation Research, vol. 36, No. 4, Dec. 2013, pp. 291-297, doi: 10.1097/MRR.0b013e3283643d5f.

Dizdar et al., "Comparative Analysis of Lateral Pharyngoplasty and Uvulopalatopharyngoplasty Techniques with Polisomnography and Epworth Sleepiness Scales", Journal of Craniofacial Surgery, vol. 26, No. 7, Oct. 2015, pp. e647-e651, doi: 10.1097/SCS.0000000000001979.

Eastwood et al., "Treating Obstructive Sleep Apnea with Hypoglossal Nerve Stimulation", Sleep, vol. 34, No. 11, Nov. 1, 2011, pp. 1479-1486, doi: 10.5665/sleep.1380.

Eckert, "Phenotypic approaches to obstructive sleep apnoea—new pathways for targeted therapy", Sleep Medicine Reviews, vol. 37, Feb. 2018, pp. 45-49, doi: 10.1016/j.smrv.2016.12.003. (Epub Dec. 18, 2016).

Garde et al., "Identifying Individual Sleep Apnea/Hypoapnea Epochs Using Smartphone-Based Pulse Oximetry", Annual International Conference of the IEEE Engineering in Medicine and Biology Society, Aug. 2016, pp. 3195-3198, doi: 10.1109/EMBC.2016.7591408.

Gillespie et al., "Upper Airway Stimulation for Obstructive Sleep Apnea: Patient-Reported Outcomes after 48 Months of Follow-up", Otolaryngology-Head and Neck Surgery, vol. 156, No. 4, 2017, pp. 765-771, doi: 10.1177/0194599817691491.

Guimaraes et al., "Effects of Oropharyngeal Exercises on Patients with Moderate Obstructive Sleep Apnea Syndrome", American Journal of Respiratory and Critical Care Medicine, vol. 179, No. 10, 2009, pp. 962-966, doi: 10.1164/rccm.200806-981oc.

Iftikhar et al., "Comparative efficacy of CPAP, MADs, Exercise-Training, and Dietary Weight Loss for Sleep Apnea: A Network Meta-Analysis", Sleep Medicine, vol. 30, Feb. 2017, pp. 7-14, doi: 10.1016/j.sleep.2016.06.001.

Javaheri et al., "Sleep Apnea: Types, Mechanisms, and Clinical Cardiovascular Consequences", Journal of the American College of Cardiology, vol. 69, No. 7, Feb. 21, 2017, pp. 841-858. doi: 10.1016/j.jacc.2016.11.069.

Jonas et al., "Screening for Obstructive Sleep Apnea in Adults: Evidence Report and Systematic Review for the US Preventive Services Task Force", JAMA, vol. 317, No. 4, 2017, pp. 415-433, doi: 10.1001/jama.2016.19635.

Kuhn et al., "Effects of CPAP and Mandibular Advancement Devices on Health-Related Quality of Life in OSA: A Systematic Review and Meta-analysis", Chest, vol. 151, No. 4, Apr. 2017, pp. 786-794, doi: 10.1016/j.chest.2017.01.020.

Kundel et al., "Impact of Portable Sleep Testing", Sleep Medicine Clinics, vol. 12, No. 1, Mar. 2017, pp. 137-147, doi: 10.1016/j.jsmc.2016.10.006.

Kuzniar, "New Approaches to Positive Airway Pressure Treatment in Obstructive Sleep Apnea", Sleep Medicine Clinics, vol. 11, No. 2, Jun. 2016, pp. 153-159, doi: 10.1016/j.jsmc.2016.03.002.

Lang et al., "Associations of Undiagnosed Obstructive Sleep Apnea and Excessive Daytime Sleepiness with Depression: An Australian Population Study", Journal of Clinical Sleep Medicine, vol. 13, No. 4, Apr. 15, 2017, pp. 575-582, doi: 10.5664/jcsm.6546. (Epub Jan. 11, 2017).

Li et al., "Pediatric Sleep Apnea Syndrome: An Update", Journal of Allergy and Clinical Immunology: In Practice, vol. 4, No. 5, Sep./Oct. 2016, pp. 852-861, doi: 10.1016/j.jaip.2016.02.022.

(56) References Cited

OTHER PUBLICATIONS

Lim et al., "Oral Appliances for Obstructive Sleep Apnoea", Cochrane Database of Systematic Reviews, vol. 1, No. CD004435, Jan. 25, 2006, 53 pgs., doi: 10.1002/14651858.CD004435.pub3.

Ljunggren et al., "Increased Risk of Heart Failure in Women with Symptoms of Sleep-Disordered Breathing", Sleep Medicine, vol. 17, Jan. 2016, pp. 32-37, doi: 10.1016/j.sleep.2015.09.018.

Mcdaid et al., "Continuous positive airway pressure devices for the treatment of obstructive sleep apnoea-hypopnoea syndrome: a systematic review and economic analysis", Health Technology Assessment, vol. 13, No. 4, Jan. 2009, 162 pgs., doi: 10.3310/hta13040.

Peppard et al., "Increased Prevalence of Sleep-Disordered Breathing in Adults", American Journal of Epidemiology, vol. 177, No. 9, Apr. 14, 2013, pp. 1006-1014, doi: 10.1093/aje/kws342.

Puri et al., "Design and Preliminary Evaluation of a Wearable Device for Mass-Screening of Sleep Apnea", 38th Annual International Conference of the IEEE Engineering in Medicine and Biology Society (EMBC), Aug. 2016, pp. 1870-1873, doi: 10.1109/embc.2016.7591085.

Robbins, "Upper Aerodigestive Tract Neurofunctional Mechanisms: Lifelong Evolution and Exercise", Head & Neck, vol. 33, No. Suppl 1, Oct. 2011, pp. S30-S36, doi: 10.1002/hed.21902.

Rousseau et al., "Effects of One-Week Tongue Task Training on Sleep Apnea Severity: A Pilot Study", Canadian Respiratory Journal, vol. 22, No. 3, May-Jun. 2015, pp. 176-178, doi: 10.1155/2015/583549.

Sharples et al., "Clinical Effectiveness and Cost-Effectiveness Results from the Randomized Controlled Trial of Oral Mandibular Advancement Devices for Obstructive Sleep Apnoea-Hypopnoea (TOMADO) and Long-Term Economic Analysis of Oral Devices and Continuous Positive Airway Pressure", Health Technology Assessment, vol. 18, No. 67, Oct. 2014, 330 pgs., doi: 10.3310/hta18670.

Subramani et al., "Understanding Phenotypes of Obstructive Sleep Apnea: Applications in Anesthesia, Surgery, and Perioperative Medicine", Anesthesia & Analgesia, vol. 124, No. 1, Jan. 2017, pp. 179-191, doi: 10.1213/ane.0000000000001546.

Svensson et al., "Plasticity in Corticomotor Control of the Human Tongue Musculature Induced by Tongue-Task Training", Experimental Brain Research, vol. 152, No. 1, 2003, pp. 42-51, doi: 10.1007/s00221-003-1517-2.

Van Eyck et al., "Sleep-disordered breathing, systemic adipokine secretion, and metabolic dysregulation in overweight and obese children and adolescents", Sleep Medicine, vol. 30, Feb. 2017, pp. 52-56, doi: 10.1016/j.sleep.2015.11.014.

Verma et al., "Oropharyngeal exercises in the treatment of obstructive sleep apnoea: our experience", Sleep and Breathing, vol. 20, No. 4, Dec. 2016, pp. 1193-1201, doi: 10.1007/s11325-016-1332-1.

Virk et al., "When continuous positive airway pressure (CPAP) fails", Journal of Thoracic Disease, vol. 8, No. 10, Oct. 1, 2016, pp. E1112-E1121, doi: 10.21037/jtd.2016.09.67.

Young et al., "Burden of Sleep Apnea: Rationale, Design, and Major Findings of the Wisconsin Sleep Cohort Study", World Medical Journal, vol. 108, No. 5, Aug. 2009, pp. 246-249.

Young et al., "The Occurrence of Sleep-disordered Breathing Among Middle-Aged Adults", New England Journal of Medicine, vol. 328, No. 17, Apr. 29, 1993, pp. 1230-1235, doi: 10.1056/nejm199304293281704.

\* cited by examiner

METHODS AND DEVICES FOR TREATING SLEEP APNEA

CROSS-REFERENCE TO RELATED APPLICATIONS

The current application is a continuation of U.S. patent application Ser. No. 16/164,539, entitled "Methods and Devices for Treating Sleep Apnea" to Douglas B. McCreery, filed Oct. 18, 2018, the disclosure of which is hereby incorporated by reference in its entirety.

BACKGROUND OF THE INVENTION

Field of the Invention

The present invention is directed generally to methods and devices for treating sleep apnea.

Description of the Related Art

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Obstructive sleep apnea ("OSA") is a chronic disease of upper airway collapse during sleep. Prevalence is estimated from as low as 1-4% of adults, to 15% of women and 30% of men, an enormous health burden, costing at least $25B/yr today. See Virk et al., "When Continuous Positive Airway Pressure (CPAP) Fails," *J Thorac Dis;* 8(10):E1112-21 (2016), Young et al., "Burden of Sleep Apnea: Rationale, Design, and Major Findings of the Wisconsin Sleep Cohort Study," *WMJ;* 108:246 (2009), and Peppard et al., "Increased Prevalence of Sleep-Disordered Breathing in Adults," *Am J Epidemiol;* 177:1006 (2013). With an increasingly obese population, prevalence of OSA is increasing in parallel, including in children, contributing to pediatric metabolic syndrome. See Van Eyck et al., "Sleep-Disordered Breathing, Systemic Adipokine Secretion, and Metabolic Dysregulation in Overweight and Obese Children and Adolescents," *Sleep Med;* 30:52-56 (2017), and Li et al., "Pediatric Sleep Apnea Syndrome: An Update." *J Allergy Clin Immunolol Pract;* 4(5):852-861 (September/October 2016).

Major risk factors include advanced age, male sex, obesity, craniofacial or upper airway soft tissue abnormalities. Pathophysiology of intermittent upper airway ("UA") obstruction, or collapse of the pharyngeal airway, despite ongoing respiratory effort, is a function of both the physiology of sleep and UA mechanics. See Danny J. Eckert, "Phenotypic Approaches to Obstructive Sleep Apnoea—New Pathways for Targeted Therapy," *Sleep Med Rev*, pii: 51087-0792(16)30154-X, Epub ahead of print, <http://dx.doi.org/10.1016/j.smrv.2016.12.003> (Dec. 18, 2016). UA factors include the effectiveness of genioglossus muscle function. See Subramani et al., "Understanding Phenotypes of Obstructive Sleep Apnea: Applications in Anesthesia, Surgery, and Perioperative Medicine," *Anesth Analg;* 124 (1):179-191 (2017).

Diagnosis of OSA is made by documenting hypopneas or apneas during sleep with polysomnography testing, and a history of daytime symptoms. See Young et al., "The Occurrence of Sleepdisordered Breathing Among Middle-Aged Adults," *N Engl J Med,* 328(17):1230-5 (1993). Increasingly, due to cost, portable monitors are used for diagnosis and wearables are entering this space. See Kundel et al., "Impact of Portable Sleep Testing," *Sleep Med Clin;* 12(1): 137-147 (2017), Garde et al., "Identifying Individual Sleep Apnea/Hypoapnea Epochs Using Smartphone-Based Pulse Oximetry," *Conf Proc IEEE Eng Med Biol Soc,* 3195-3198 (2016), and Puri et al., "Design and Preliminary Evaluation of a Wearable Device for Mass-Screening of Sleep Apnea," *Conf Proc IEEE Eng Med Biol Soc,* 1870-1873 (2016).

Most OSA is considered mild to moderate. The American Academy of Sleep Medicine (AASM) defines mild OSA as an apnea-hypopnea index ("AHI") of 6-14 events per hour; moderate OSA as an AHI of 15-30 events per hour; and severe OSA as an AHI of greater than 30 events per hour. See American Academy of Sleep Medicine, *International Classification of Sleep Disorders,* 3rd ed, American Academy of Sleep Medicine, Darien, IL 2014.

Nevertheless, OSA results in daytime somnolence, poor cognitive performance, depression, sympathetic activation, and increased morbidity from cardiac disease including heart failure, arrhythmias, and stroke. See Lang et al., "Associations of Undiagnosed Obstructive Sleep Apnea and Excessive Daytime Sleepiness with Depression: An Australian Population Study," *J Clin Sleep Med*, pii: jc-00336-16, Epub ahead of print (Jan. 11, 2017), Ljunggren et al., "Increased Risk of Heart Failure in Women with Symptoms of Sleep-Disordered Breathing," *Sleep Med,* 17:32-37 (January 2016), and Javaheri et al., "Sleep Apnea: Types, Mechanisms, and Clinical Cardiovascular Consequences," *J Am Coll Cardiol,* 69(7):841-858 (Feb. 21, 2017).

While OSA is common, its treatment options are limited and currently available treatment options for OSA are suboptimal. For example, continuous positive airway pressure ("CPAP"), including nasal CPAP, is the standard therapy and overall the best non-surgical treatment, but does not cure OSA. CPAP works by forcing sufficient pressure into the airway to stent it open. CPAP is often not well-tolerated leading to poor compliance. For example, CPAP complications include dry nose, dry mouth, dry throat, eye irritation, face irritation, and abdominal bloating. Further, meta-analyses show that while CPAP positively affects quality of life, CPAP does not significantly reduce OSA-related mortality. See Jonas et al., "Screening for Obstructive Sleep Apnea in Adults: Evidence Report and Systematic Review for the US Preventive Services Task Force," *JAMA,* 317(4):415-433 (2017). Improved CPAP modes with customized masks, humidified air, and/or automatic pressure adjustment can help with compliance. See Tomasz J. Kuzniar, "New Approaches to Positive Airway Pressure Treatment in Obstructive Sleep Apnea," *Sleep Med Clin,* 11:153-159 (2016).

Another example includes mandibular advancement devices ("MADs"), which are useful in some OSA patients with milder disease who do not tolerate CPAP. See Kuhn et al., "Effects of CPAP and MADs on Healthrelated Quality of Life in OSA: A Systematic Review and Meta-Analysis," *Chest,* pii:S0012-3692(17)30038-7, doi: [Epub ahead of print] (2017), and Lim et al., "Oral Appliances for Obstructive Sleep Apnoea," *Cochrane Database Syst Rev,* 1:CD004435 (2006). However, MADs overall clinical and cost-effectiveness have been questioned in meta-analyses. See McDaid et al., "Continuous Positive Airway Pressure Devices for the Treatment of Obstructive Sleep Apnoea—Hypopnoea Syndrome: A Systematic Review and Economic Analysis," *Health Technol Assess,* 13(4), http://dx.doi.org/

10.3310/hta13040 (2009). Unfortunately, MADs can cause jaw discomfort, gum discomfort, mouth discomfort, tooth damage, and mouth ulcers. See Sharples et al., "Clinical Effectiveness and Cost-Effectiveness Results from the Randomized Controlled Trial of Oral Mandibular Advancement Devices for Obstructive Sleep Apnoea-Hypopnoea (TOMADO) and Long-Term Economic Analysis of Oral Devices and Continuous Positive Airway Pressure," *Health Technology Assessment*, 18(67), DOI 10.3310/hta18670 (2014).

Considerably less experience is available for upper airway electrical stimulation devices which require a surgical procedure to implant the device. Notably these electrical stimulation devices are proving effective in moderate to severe OSA. See Eastwood et al., "Treating Obstructive Sleep Apnea with Hypoglossal Nerve Stimulation," *Sleep*, 34(11): 1479-86 (Nov. 1, 2011) and Gillespie et al., "Upper Airway Stimulation for Obstructive Sleep Apnea: Patient-Reported Outcomes after 48 Months of Follow-up," *Otolaryngol Head Neck Surg*, 156(4):765-771 (2017).

Weight loss and exercise training are adjunctive therapies for OSA, but difficult to sustain. See Iftikhar et al., "Comparative Efficacy of CPAP, MADs, Exercise-Training, and Dietary Weight Loss for Sleep Apnea: A Network Meta-Analysis," *Sleep Med*, 30:7-14 (2017). Patient positioning during sleep can also be helpful. Less commonly, surgical procedures correcting nasal or airway anatomic features can treat OSA. See Dizdar et al., "Comparative Analysis of Lateral Pharyngoplasty and Uvulopalatopharyngoplasty Techniques with Polisomnography and Epworth Sleepiness Scales," *J Craniofac Surg*, 26(7):e647-e651 (October 2015).

However, each of the currently available treatment options mentioned above has its drawbacks. Thus, a need exists for methods and devices for treating OSA. The present application provides these and other advantages as will be apparent from the following detailed description and accompanying figures.

BRIEF DESCRIPTION OF THE SEVERAL VIEWS OF THE DRAWING(S)

Exemplary embodiments are illustrated in referenced figures. It is intended that the embodiments and figures disclosed herein are to be considered illustrative rather than restrictive.

Like reference numerals have been used in the figures to identify like components.

DETAILED DESCRIPTION OF THE INVENTION

As used herein, the terms "treatment" and "treating" refer to both therapeutic treatment and prophylactic or preventative measures, wherein the object is to prevent or decrease (lessen) the targeted condition or disorder even if the treatment or prevention is ultimately unsuccessful. Those in need of treatment include those already afflicted with the disorder as well as those prone to have the disorder or those in whom the disorder is to be prevented or treated. For example, in obstructive sleep apnea ("OSA") treatment, a therapeutic apparatus may decrease the number of apneic and/or hypoxic episodes, which may decrease the symptoms and/or sequelae associated with OSA.

Figure 1:
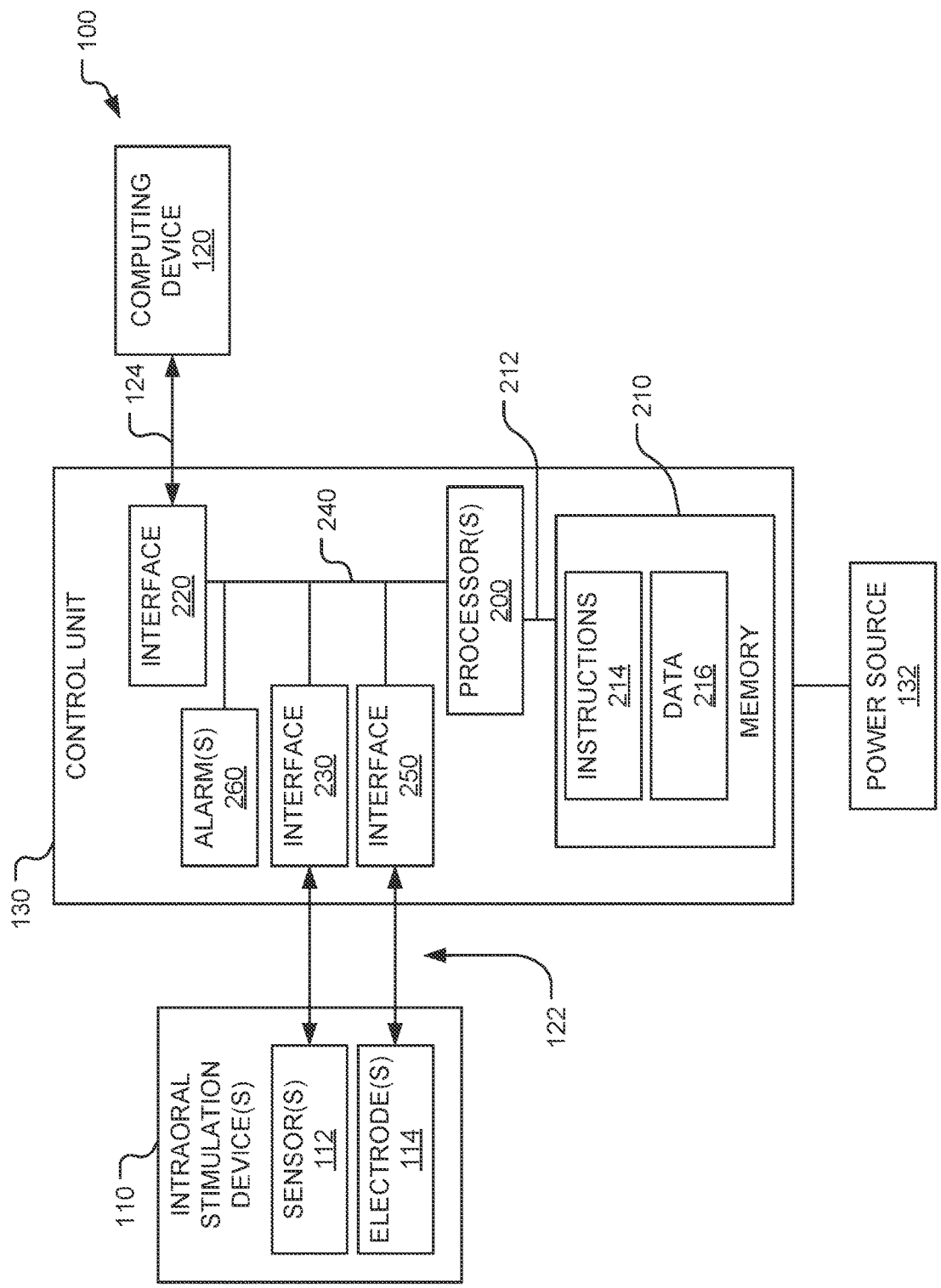
FIG. 1 is a block diagram of a system for treating sleep apnea in a patient.
Figure 4:
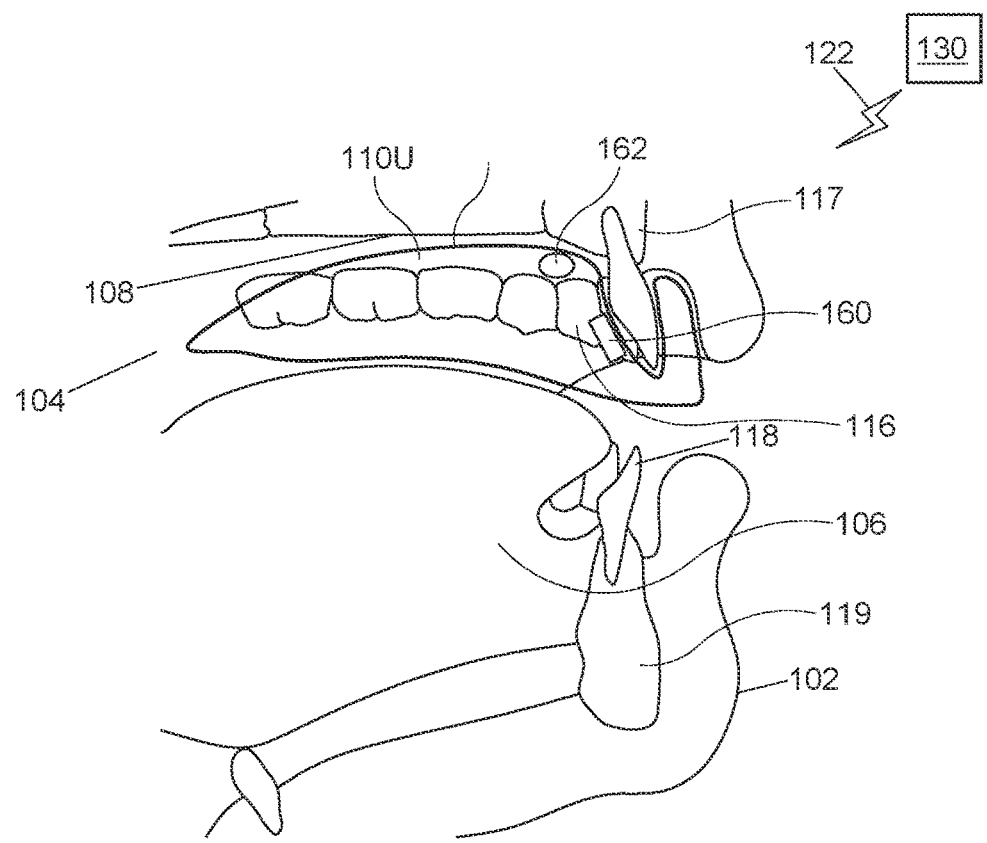
FIG. 4 is a side cross-sectional view of an exemplary wireless embodiment of an upper bite block illustrated in the patient's mouth.
Figure 8:
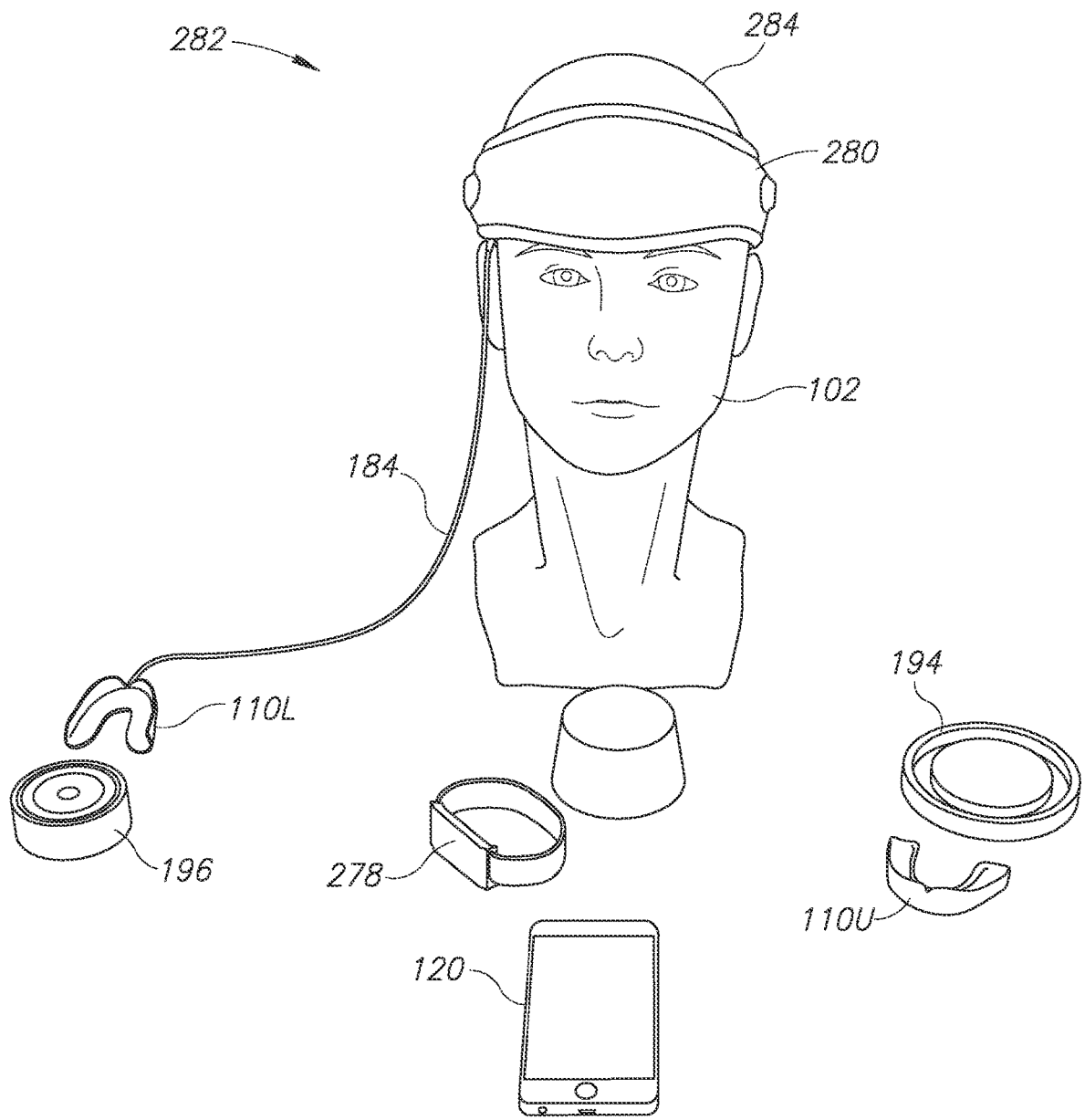
FIG. 8 is a perspective view of the patient wearing a headband that include a control unit and intraoral stimulation device(s) of the system of FIG. 1.

FIG. 1 illustrates a system 100 for treating sleep apnea in a patient 102 (see FIGS. 4 and 8). Referring to FIG. 4, obstruction of the upper airway ("UA") 104 that occurs in OSA is caused by a reduction in the tone of the muscles of the UA 104 during sleep, accompanied by prolapse of the base of the tongue 106 into the UA 104. Fortunately, this may be prevented by activating the muscles that extend the tongue 106. These muscles may be activated by direct electrical stimulation of the nerves effecting tongue extension. As explained below, these muscles may also be activated by an acquired tongue extension reflex that is acquired and maintained by electrical stimulation of the hard palate 108.

Referring to FIG. 1, the system 100 may be characterized as being a biofeedback training system. The system 100 includes one or more intraoral stimulation devices 110 operated by a control unit 130. The control unit 130 is powered by a power source 132 (e.g., a battery). Depending upon the implementation details, the intraoral stimulation device(s) 110 may also be powered by the power source 132. The intraoral stimulation device(s) 110 may be connected by one or more wired and/or wireless connections 122 to the control unit 130. The control unit 130 may be connected by one or more wired and/or wireless connections 124 to an external computing device 120 (e.g., a cellular telephone, tablet computing device, laptop computer, and the like).

The intraoral stimulation device(s) 110 are configured to deliver electrical stimulation to the hard palate 108 (see FIGS. 4 and 9B) of the patient 102 (see FIGS. 4 and 8) when the tongue 106 (see FIGS. 4 and 5) is in an undesirable position in which the tongue 106 may obstruct the UA 104

(see FIG. 4). The electrical stimulation delivered to the tongue 106 (see FIGS. 4 and 5) causes the tongue 106 to move forwardly to a desirable position whereat the tongue 106 no longer obstructs the UA 104 (see FIG. 4).

A brief discussion of the electrophysiology of sensory nerves of the skin and integument of the mouth may be helpful. A range of somatosensory percepts is served by various types of sensory nerve fibers which originate in the skin and lining of the mouth. The sensations of touch and pressure are mediated by large nerve fibers with specialized endings. Pricking pain is mediated by smaller delta fibers, and burning pain is mediated by the smallest nerve fibers (C-Fibers). See Vernon M., "Chapter 10: Mechanisms in Somaesthesia and Pain in Sensory Sensibilities," Mountcastle Medical Physiology, Volume 1 (1974).

While nerve fibers are normally activated by touch, pressure, or injury, they also can be activated by electrical stimulation. For example, a train of electrical pulses, each pulse having a current amplitude (I) and a duration (D), may be used. The following Hill equation may be used to determine values for the current amplitude I and the duration D that will generate an electrical stimulus pulse that is just adequate to activate a nerve fiber, and thus elicit the percepts served by that class of fibers:

$$I_{th} = I_r/(1-e^{-D/T}).$$

In the Hill equation, $I_{th}$ is the threshold current just sufficient to activate the fiber, $I_r$ is the nerve fiber's rheobase current, T is the fiber's chronaxie, and D is the duration of the stimulus pulse that is just adequate to activate the fiber. It is well established that $I_r$ and T are greater for smaller nerve fibers. Thus, when a train of electrical pulses is applied to the skin or to the lining of the mouth, and the current amplitude I is small and/or the pulse duration D is short, only the larger nerve fibers that mediate the sensation of touch or pressure will be activated. As duration D and/or current amplitude I are progressively increased, the A-delta nerve fibers mediating pricking pain will be recruited and the percept will transition from that of touch or tapping to pricking pain, and finally, to burning pain as the current amplitude I and/or duration D of the stimulus pulses becomes sufficient to activate C-fibers.

Referring to FIG. 4, the tongue 106 moves forwardly and reflexively in response to electrical stimulation. While stronger electrical stimuli may be needed initially to cause the tongue 106 to move, the stimuli may be reduced as the tongue 106 is trained by the system 100 (see FIG. 1). Thus, the system 100 may lower a threshold of the conditioned tongue-forward reflex in response to electrical stimulation, independently increase UA muscle tone, and/or improve OSA. See Robbins J., "Upper Aerodigestive Tract Neurofunctional Mechanisms: Lifelong Evolution and Exercise," Head Neck, 33 Suppl 1:S30-6 (2011), Chwieśko-Minarowska et al., "Rehabilitation of Patients with Obstructive Sleep Apnea Syndrome," Int J Rehabil Res, 36(4):291-297 (2013), Rousseau et al., "Effects of One-Week Tongue Task Training on Sleep Apnea Severity: A Pilot Study," Can Respir J, 22(3):176-8 (May-June 2015), Svensson et al., "Pleasticity in Corticomotor Control of the Human Tongue Musculature Induced by Tongue-Task Training," Exp Brain Res, 152(1):42-51 (2003), Verma et al., "Oropharyngeal Exercises in the Treatment of Obstructive Sleep Apnoea: Our Experience," Sleep Breath, 20(4):1193-1201 (December 2016), and Guimaraes et al., "Effects of Oropharyngeal Exercises on Patients with Moderate Obstructive Sleep Apnea Syndrome," Am J Resp Crit Care Med, 179:962-966 (2009). It is possible that extended training with the system 100 could reduce OSA symptoms (and reduce the need for therapy).

INTRAORAL STIMULATION DEVICE(S)

Referring to FIG. 1, the intraoral stimulation device(s) 110 may be characterized as being a patient interface that includes one or more sensors 112 and one or more electrodes 114. The intraoral stimulation device(s) 110 may include an upper (maxillary) bite block 110U (see FIGS. 2-5) configured to be positioned on the patient's upper teeth 116 (see FIGS. 4 and 5) of a patient's maxilla (upper jaw) 117 (see FIG. 4) and/or a lower (mandibular) bite block 110L (see FIGS. 6 and 7) configured to be positioned on the patient's lower teeth 118 (see FIGS. 6 and 7) of a patient's mandible (lower jaw) 119 (see FIG. 4).

Referring to FIG. 8, the upper and lower bite blocks 110U and 110L may each be implemented as a dental fixture, a maxillary dental mouthpiece, and the like. By way of a non-limiting example, the upper and lower bite blocks 110U and 110L may be substantially similar to bite blocks used for teeth whitening and may be custom-fitted by a dentist. The upper and lower bite blocks 110U and 110L may be constructed from a flexible material (such as a silicone) that is custom molded to a patient's teeth and jaw. For example, the upper (maxillary) bite block 110U may be fabricated using a tooth tray that fits the patient's upper palate arch and is adapted to the patient's individual upper teeth 116 (see FIGS. 4 and 5). The lower bite block 110L may substantially cover the entire mandibular arch. Alternatively, the lower bite block 110L may be made smaller so that it sits only on front ones of the lower teeth 118 and not on the entire mandibular arch.

The upper and lower bite blocks 110U and 110L may be constructed from a flexible material that may be transparent at least in the vicinity of the sensor(s) 112 (see FIG. 1). However, this is not a requirement. In alternate embodiments, the material may be translucent or opaque.

Referring to FIG. 4, to keep the UA 104 open, the tongue 106 should be positioned just behind the teeth 116 and 118. Referring to FIG. 1, the sensor(s) 112 are configured to sense the position of the tongue 106 (see FIGS. 4 and 5) inside the patient's mouth. Each of the sensor(s) 112 may be configured to monitor the position of the tongue 106 (see FIG. 4) and/or the force exerted by the tongue 106 (particularly, the tip of the tongue 106) against the sensor. The sensor(s) 112 may be implemented as sensing electrodes. Examples of suitable tongue position sensors are provided in U.S. Pat. No. 8,249,723, which is incorporated herein by reference in its entirety. By way of non-limiting examples, each of the sensor(s) 112 may have an emitter and a detector in a transparent encapsulant separated by an opaque partition. The emitter may be an infrared emitter and the detector may be an infrared detector.

Referring to FIG. 1, if the patient 102 (see FIGS. 4 and 8) breathes primarily through the patient's nose (instead of through the patient's mouth) during sleep, the sensor(s) 112 of the upper bite block 110U (see FIGS. 2-5) may be use to sense the position of the tongue 106 (see FIGS. 4 and 5) inside the patient's mouth. On the other hand, if the patient 102 breaths primarily through the patient's mouth (instead of through the patient's nose, which is commonly referred to as "mouth breathing") during sleep, the sensor(s) 112 of the lower bite block 110L (see FIGS. 6 and 7) may be used to sense the position of the tongue 106 (see FIGS. 4 and 5) inside the patient's mouth. Thus, the lower bite block 110L (see FIGS. 6 and 7) may only be needed by mouth breathing patients. In other words, the patient 102 may use the upper bite block 110U (see FIGS. 2-5) or both the upper and lower bite blocks 110U and 110L (see FIGS. 6 and 7) depending upon how the patient 102 breathes during sleep.

The electrode(s) 114 are configured to deliver electrical stimulation to a structure in the patient's mouth (e.g., the hard palate 108 illustrated in FIG. 4). By way of a non-limiting example, the electrode(s) 114 may be configured to deliver direct electrical stimulation to the integument of the hard palate 108 (see FIGS. 4 and 9B). The direct electrical stimulation applied by the electrode(s) 114 of the intraoral stimulation device(s) 110 cause the tongue 106 (see FIGS. 4 and 5) to move forwardly (or protrude to an anterior position), maintain the tongue 106 in an anterior position, and/or maintain an increased tone in the tongue extensor muscles during sleep, thereby avoiding obstruction of the UA 104 (see FIG. 4) during sleep. As explained below, the intensity of the simulation delivered by the electrode(s) 114 may increase over a predetermined time period (e.g., about 5 seconds to about 7 seconds). Thus, when the tongue 106 does not move, the intensity increases until the tongue 106 moves forwardly.

Figure 2:
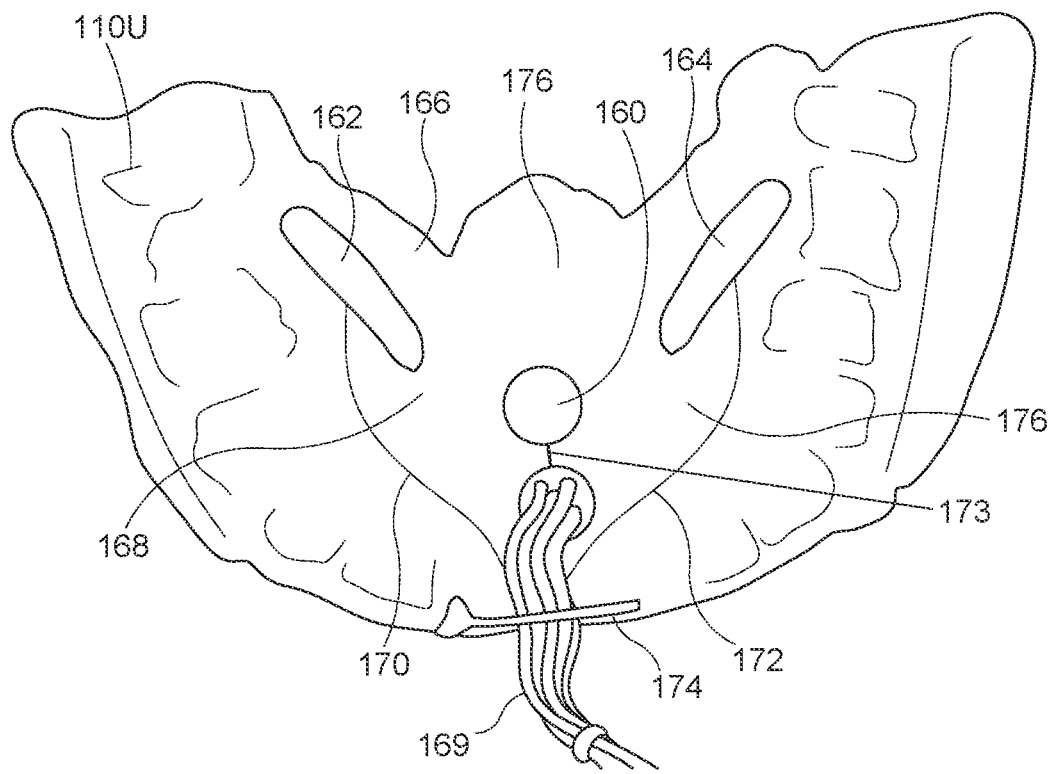
FIG. 2 is a top view of an exemplary wired embodiment of an upper bite block that includes stimulating electrodes and a tongue position sensor and is configured to fit over the patient's maxillary teeth.

FIG. 2 is a top view of an exemplary embodiment of the upper (maxillary) bite block 110U. Referring to FIG. 2, the sensor(s) 112 (see FIG. 1) of the upper bite block 110U include a tongue position sensor 160 and the electrode(s) 114 (see FIGS. 1, 9A, and 9B) of the upper bite block 110U include a pair of stimulating electrodes 162 and 164. When the upper bite block 110U is positioned inside the patient's mouth, the tongue position sensor 160 is positioned close to the front of the patient's tongue 106 and the stimulating electrodes 162 and 164 are positioned close to and contact the hard palate 108 (see FIGS. 4 and 9B). The stimulating electrodes 162 and 164 are maintained in a reliable but comfortable contact with the hard palate 108 (see FIGS. 4 and 9B). The tongue position sensor 160 and the stimulating electrodes 162 and 164 may be embedded in the upper (maxillary) bite block 110U. Referring to FIG. 4, the stimulating electrodes 162 and 164 (see FIGS. 2 and 5) are configured to deliver stimulation to the anterior hard palate 108 when the tongue position sensor 160 detects the tongue 106 is positioned away from the upper teeth 116, which means the tongue 106 is in the patient's UA 104.

Figure 9A:
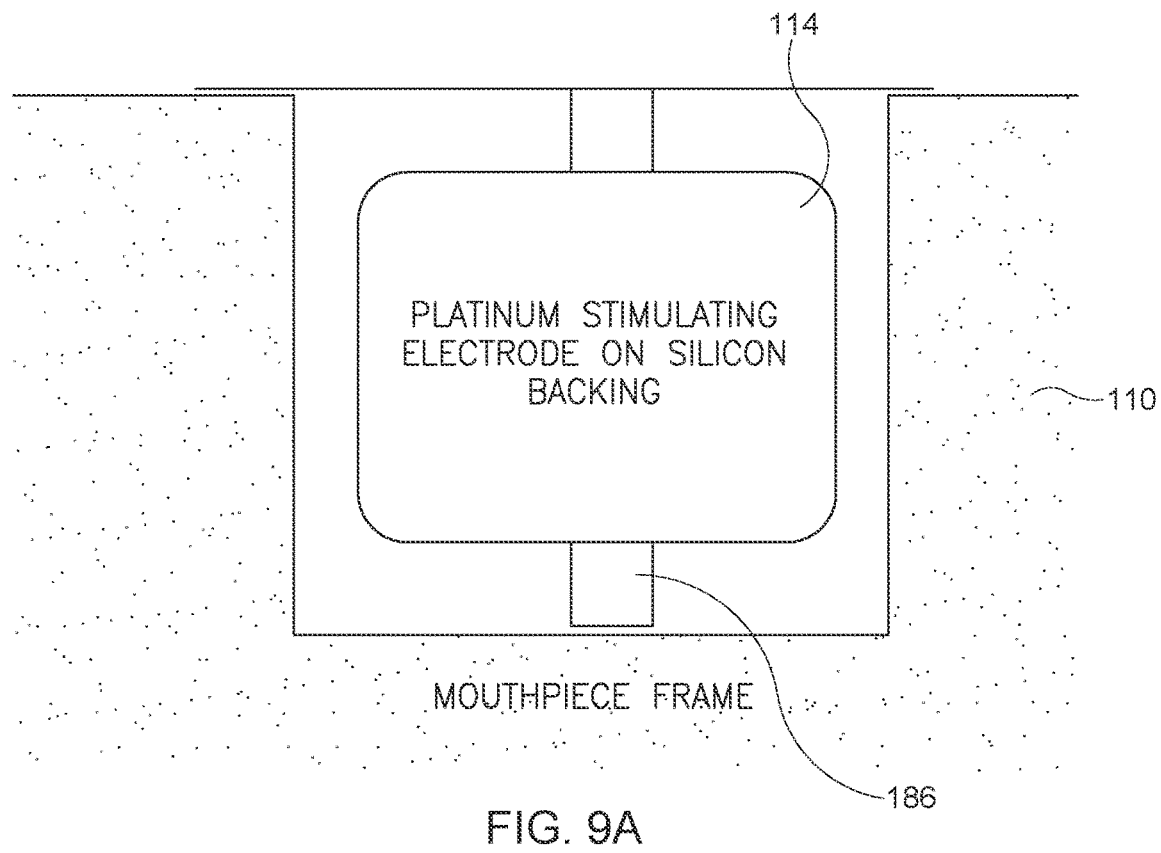
FIG. 9A is a side view of an exemplary electrode pivotally connected to one of the intraoral stimulation device(s) of the system of FIG. 1.
Figure 9B:
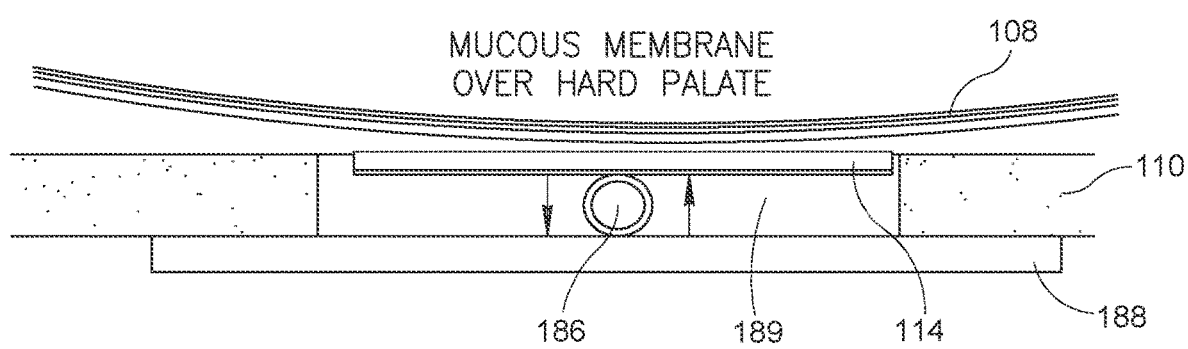
FIG. 9B is a cross-sectional view of the electrode of FIG. 9A.

Referring to FIG. 2, the upper bite block 110U has an upper surface 166 that may include a palate region 168 configured to contact the patient's hard palate 108 (see FIGS. 4 and 9B). In the embodiment illustrated, the palate region 168 includes the stimulating electrodes 162 and 164 positioned to contact the patient's hard palate 108 (see FIGS. 4 and 9B). The stimulating electrodes 162 and 164 may be connected to electrical leads 170 and 172, respectively, which supply power to the stimulating electrodes 162 and 164. By way of a non-limiting example, the stimulating electrodes 162 and 164 may be constructed from platinum.

Figure 3:
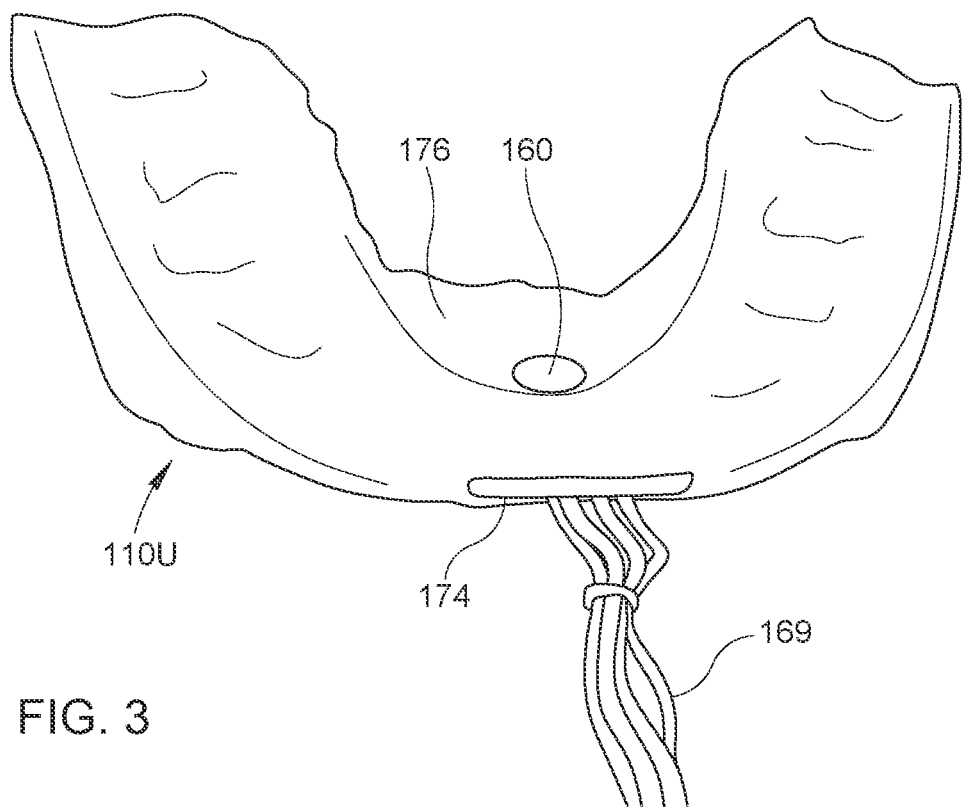
FIG. 3 is a bottom view of the upper bite block of FIG. 2.

FIG. 3 is a bottom view of the upper (maxillary) bite block 110U. Referring to FIG. 3, the tongue position sensor 160 is located near a front portion 174 of the upper bite block 110U in a generally upwardly concave contoured portion 176. The tongue position sensor 160 may detect or monitor the position of the tongue 106 or the force exerted by the tongue 106 against the tongue position sensor 160. The tongue position sensor 160 may be connected to an electrical lead 173, which supplies power to the tongue position sensor 160.

FIGS. 2 and 3 illustrate a wired implementation of the upper (maxillary) bite block 110U. In such an embodiment, referring to FIG. 1, the control unit 130 and the power source 132 may both be external to the upper bite block 110U (see FIGS. 2 and 3) and the connection(s) 122 may include control and power wiring 169 (see FIGS. 2 and 3). Referring to FIG. 2, the wiring 169 extends from the upper bite block 110U and is connected to the external control unit 130 (see FIGS. 1, 4, 5, and 7) and the power source 132 (see FIG. 1). The wiring 169 carries tongue position information from the tongue position sensor 160 (via the electrical lead 173) to the external control unit 130. The wiring 169 also conducts electrical power from the power source 132 to the tongue position sensor 160 via the electrical lead 173. The wiring 169 carries a stimulation signal from the external control unit 130 to the stimulating electrodes 162 and 164 (via the electrical leads 170 and 172).

Figure 5:
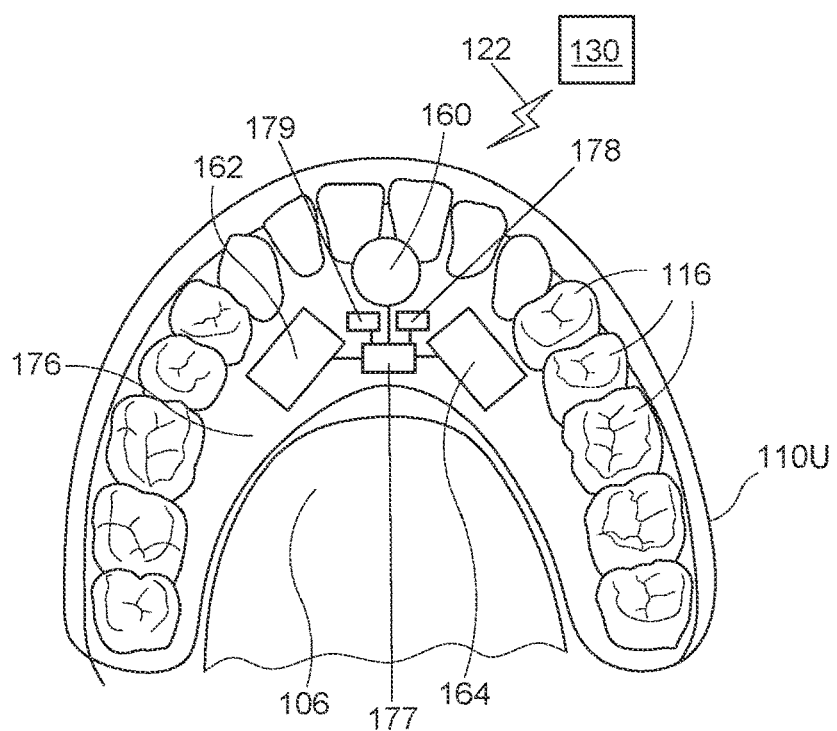
FIG. 5 is a bottom view of the upper bite block of FIG. 4 illustrated in the patient's mouth.

Alternatively, FIGS. 4 and 5 illustrate a wireless implementation of the upper (maxillary) bite block 110U. Referring to FIG. 5, in such an embodiment, the upper bite block 110U includes onboard wireless transponder 177 and an onboard battery 178 that may be molded into the upper bite block 110U. In this embodiment, the connection(s) 122 may be implemented as a wireless connection between the onboard wireless transponder 177 and the control unit 130. The onboard battery 178 is configured to provide power to the tongue position sensor 160, the stimulating electrodes 162 and 164, and the onboard wireless transponder 177. The battery 178 may be charged wirelessly, such as by inductive charging or by other technology. The tongue position sensor 160 is configured to detect and/or monitor tongue position information and transmit this information to the onboard wireless transponder 177. The onboard wireless transponder 177, which is wirelessly connected to the control unit 130, is configured to wirelessly communicate the tongue position information to the control unit 130. The control unit 130 receives this information and wirelessly sends stimulation instructions to the onboard wireless transponder 177. The onboard wireless transponder 177 may be connected to a signal-generating device 179 that is configured to generate a stimulation signal based on the stimulation instructions. The stimulation signal is powered by the battery 178 and delivered to the stimulating electrodes 162 and 164, which deliver the stimulation signal to the hard palate 108 (see FIG. 4). Thus, the control unit 130 is configured to receive the tongue position information (directly or wirelessly) and determine whether to deliver the stimulation signal to the patient 102.

Referring to FIG. 9A, each of the electrode(s) 114 (e.g., the stimulating electrodes 162 and 164 illustrated in FIGS. 2 and 5) may be attached to one of the intraoral stimulation device(s) 110 (e.g., the upper bite block 110U illustrated in FIGS. 2-5 and 8) in a manner that allows them to maintain stable and reliable but comfortable contact with the patient's hard palate 108 (see FIGS. 4 and 9B). FIGS. 9A and 9B illustrate an exemplary implementation of one of the electrode(s) 114 (e.g., the electrode 162 illustrated in FIG. 2) pivotally connected to one of the intraoral stimulation device(s) 110. Each of the electrode(s) 114 may be pivotally connected to a different pivot member 186 that allows each of the electrode(s) 114 to pitch and pivot to lie flat against the integument of the hard palate 108 (see FIGS. 4 and 9B). By way of a non-limiting example, the pivot member 186 may be implemented as a flexible silicone supporting tube (e.g., constructed of medical grade silicone rubber) or other mechanism(s) (e.g., springs, ball joints, silicon arms, and the like) configured to allow the electrode 114 to pivot relative to the intraoral stimulation device 110.

In the embodiment illustrated, the pivot member 186 is connected to a backing plate 188 that is connected to the intraoral stimulation device 110. A pivot space 189 is defined between the electrode 114 and the backing plate 188. The pivot space 189 allows the electrode 114 to pivot to position the top of the electrode 114 generally flush with the upper surface (e.g., the upper surface 166 illustrated in FIG. 2) of the intraoral stimulation device 110 in its palate region 168 (see FIG. 2). The pivot space 189 also allows the electrode 114 to pivot to lie flat against the hard palate 108 (see FIGS. 4 and 9B). Referring to FIG. 9B, the pivot member 186 allows the electrode 114 to maintain uniform contact with the hard palate 108, even when the patient 102 bites or sucks against the intraoral stimulation device 110 (e.g., a night guard). The intraoral stimulation device 110 may be implemented as a night guard of the type used widely to treat bruxism. Such a night guard may be custom fitted to the patient 102 by a qualified dentist with experience fitting these devices.

Figure 7:
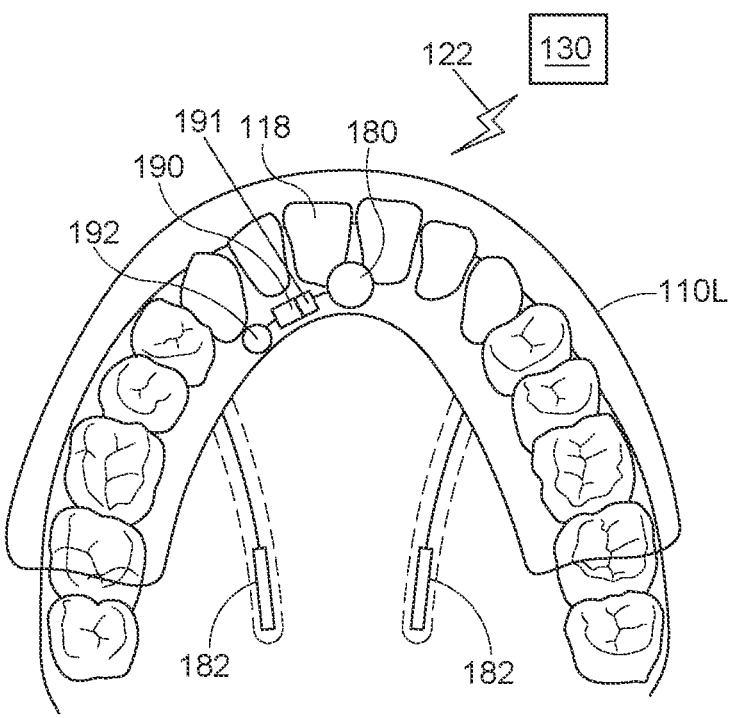
FIG. 7 is a bottom view of an exemplary wireless embodiment of a lower bite block illustrated in the patient's mouth.

Referring to FIG. 7, as mentioned above, the lower (mandibular) bite block 110L may be used in conjunction with the upper (maxillary) bite block 110U (see FIGS. 2-5) and is particularly useful for a mouth breather, whose tongue 106 (see FIGS. 4 and 5) may be closer to the lower teeth 118 than the upper teeth 116 (and the tongue position sensor 160 of the upper bite block 110U). The sensor(s) 112 (see FIG. 1) of the lower bite block 110L include a tongue position sensor 180 (e.g., a sensing electrode) and the electrode(s) 114 (see FIGS. 1, 9A, and 9B) of the lower bite block 110L may include one or more stimulating electrodes 182. The tongue position sensor 180 and the stimulating electrode(s) 182 may be embedded in or otherwise attached to the lower bite block 110L. The tongue position sensor 180 is positioned behind front ones of the lower teeth 118 and configured to detect whether the tongue 106 (see FIGS. 4 and 5) is in the desired (forward) position, or is retracted back towards the UA 104 (see FIG. 4).

In the embodiment illustrated, the stimulating electrode(s) 182 have been implemented as sublingual electrodes that are configured to excite the tongue extensor muscle directly, as described in U.S. Pat. Nos. 8,249,723, 8,359,108, and 8,774,943, each of which is incorporated herein by reference in its entirety. By way of non-limiting examples, the sublingual electrodes may be substantially identical to electrodes 403 of U.S. Pat. Nos. 8,249,723, 8,359,108, and 8,774,943 that are configured to deliver electrical stimulation to the tongue extensor muscles.

Figure 6:
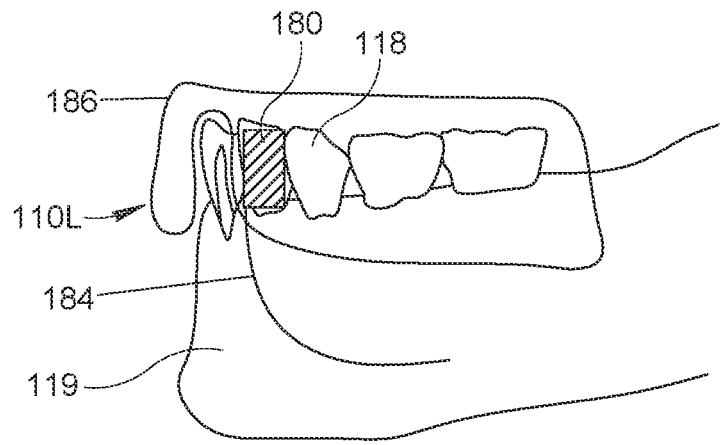
FIG. 6 is a side view of an exemplary wired embodiment of a lower bite block illustrated in the patient's mouth.

Alternatively and/or additionally, the stimulating electrodes 162 and 164 (see FIGS. 2 and 5) may deliver stimulation to the anterior hard palate 108 (see FIGS. 4 and 9B) when the tongue position sensor 180 detects the tongue 106 (see FIGS. 4 and 5) is positioned away from the lower teeth 118 (see FIG. 6). In such embodiments, the stimulating electrode(s) 182 may be omitted.

FIG. 6 illustrates a wired implementation of the lower bite block 110L. In such an embodiment, the control unit 130 (see FIGS. 1, 4, 5, and 7) and the power source 132 (see FIG. 1) may both be external to the lower bite block 110L and the connection(s) 122 (see FIG. 1) may include control and power wiring 184 (see FIG. 8). The wiring 184 (see FIG. 8) extends from the lower bite block 110L and is connected to the external control unit 130 (see FIGS. 1, 4, 5, and 7) and the power source 132 (see FIG. 1). The wiring 184 (see FIG. 8) carries tongue position information from the tongue position sensor 180 to the external control unit 130 and conducts electrical power to the tongue position sensor 180 from the power source 132. The wiring 184 (see FIG. 8) may carry a stimulation signal from the external control unit 130 to the stimulating electrode(s) 182 (see FIG. 7), when present. Referring to FIG. 2, alternatively and/or additionally, the wiring 169 may carry the stimulation signal to the stimulating electrodes 162 and 164, which deliver the stimulation to the anterior hard palate 108. The stimulation signal is also powered by the power source 132.

FIG. 7 illustrates a wireless implementation of the lower bite block 110L. In such an embodiment, the lower bite block 110L may include an onboard wireless transponder 190 and an onboard battery 192 that may be molded into the lower bite block 110L. In this embodiment, the connection(s) 122 may be implemented as a wireless connection between the onboard wireless transponder 190 and the control unit 130. The onboard battery 192 is configured to provide power to the mandibular tongue position sensor 180, the stimulating electrode 182, the onboard wireless transponder 190, and, when present, the stimulating (sublingual) electrode(s) 182. The onboard battery 192 may be charged wirelessly, such as by inductive charging or by other technology. The tongue position sensor 180 is configured to detect and/or monitor tongue position information. The tongue position sensor 180 transmits this information to the onboard wireless transponder 190. The onboard wireless transponder 190 is configured to wirelessly communicate the tongue position information to the control unit 130. The control unit 130 receives this information and wirelessly sends stimulation instructions to the onboard wireless transponder 190. The onboard wireless transponder 190 may be connected to signal generating device 191 that is configured to generate a stimulation signal based on the stimulation instructions. The stimulation signal is powered by the battery 192 and delivered to the stimulating electrode(s) 182, which deliver the stimulation signal to the tongue extensor muscle.

Referring to FIG. 5, alternatively and/or additionally, the control unit 130 may send instructions to the onboard wireless transponder 177, which is connected to the signal-generating device 179. The signal-generating device 179 is configured to generate a stimulation signal based on the stimulation instructions, and sends the stimulation signal to the stimulating electrodes 162 and 164, which deliver the stimulation to the anterior hard palate 108.

Thus, referring to FIG. 7, the control unit 130 is configured to receive the tongue position information (directly or wirelessly) from the lower bite block 110L and determine whether to deliver the stimulation signal to the patient 102 (see FIGS. 4 and 8).

The mandibular tongue position sensor 180 and the maxillary tongue position sensor 160 (see FIGS. 2-5) may both be connected to the control unit 130 at the same time. In such embodiments, the control unit 130 may determine based on the tongue position information received from the sensors 180 and 160 whether the tongue 106 is closer to the mandibular tongue position sensor 180 or the maxillary tongue position sensor 160. In this way, the control unit 130 may use the greater (or stronger) of the two signals (including the tongue position information) received from the two tongue position sensors 180 and 160 to determine whether to deliver electrical stimulation to the patient 102 (see FIGS. 4 and 8).

Control Unit

The control unit 130 may be implemented using a circuit board (e.g., a custom signal interface board) with components implementing a wired or wireless control unit. While in the embodiment illustrated, the control unit 130 is illustrated as being a separate component, in alternate embodiments, the control unit 130 may be a component of either the computing device 120 and/or the intraoral stimulation device(s) 110. For example, referring to FIGS. 4 and 5, in a wireless implementation illustrated, the control unit 130 may be a component of the upper bite block 110U. Referring to FIG. 7, by way of another non-limiting example, the control unit 130 may be a component of the lower bite block 110L.

Referring to FIG. 1, the control unit 130 is connected to the intraoral stimulation device(s) 110 and may both receive signals from the sensor(s) 112 and send electrical stimulation to the electrode(s) 114. As mentioned above, the control unit 130 is powered by the power source 132 (e.g., by a battery). The power source 132 may be a component of the control unit 130 and/or a separate component.

The control unit 130 may include one or more processors 200, which may be implemented by any suitable technology, such as a microprocessor, microcontroller, application-specific integrated circuit (ASIC), digital signal processor ("DSP"), or the like. The processor(s) 200 may be integrated into an electrical circuit, similar to a "motherboard" of a general-purpose computer that supplies power to the processor(s) 200 and otherwise supports its function.

The processor(s) 200 may include internal memory or have memory 210 coupled thereto. The memory 210 may be coupled to the processor(s) 200 by an internal bus 212. The memory 210 is a computer readable medium that includes instructions 214 or computer executable components that are executed by the processor(s) 200. The memory 210 may also store data 216. The memory 210 may include random access memory (RAM) and read-only memory (ROM). The instructions 214 and the data 216 may control the operation of the processor(s) 200. The instructions 214 may include software and/or firmware configured to operate a tongue sensor/stimulation feedback loop. The memory 210 may also include a basic input/output system (BIOS), which contains the basic routines that help transfer information between elements within the control unit 130. The control unit 130 is not limited by the specific hardware component(s) used to implement the processor(s) 200 or the memory 210 components of the control unit 130.

The instructions 214 are executable by the processor(s) 200 and instruct the processor(s) 200 to process and/or analyze the signals received by the sensor(s) 112. The instructions 214 may instruct the processor(s) 200 to generate electrical stimulus and deliver that stimulus to the electrode(s) 114, which deliver the stimulus to the patient 102 (see FIGS. 4 and 8). The instructions 214 executed by the control unit 130 may monitor and record tongue force applied to the sensor(s) 112 as well as tongue position. These instructions may include computer readable software components or modules stored in the memory 210.

The control unit 130 may also include an external device interface 220 permitting a user (e.g., the patient 102, and/or a medical professional) to enter control commands, such as a command triggering the delivery of the electrical pulses, commands providing new instructions to be executed by the processor(s) 200, commands changing parameters related to electrical pulses delivered by the control unit 130, and the like, into the control unit 130. The external device interface 220 may include a wireless user input device. The external device interface 220 may include an antenna (not shown) for receiving and transmitting a signal, such as a radio frequency (RF) signal, to and from the control unit 130. The control unit 130 may also include software components for interpreting the commands and executing control commands included in a command signal. These software components may be stored in the memory 210. The connection 124 may be implemented using WiFi, Bluetooth, or similar wireless communication standards. In such embodiments, the control unit 130 is configured to communicate with the computing device 120 (e.g., a cellular telephone) using at least one of these standards.

The control unit 130 includes a signal interface 230 coupled the sensor(s) 112 (e.g., the tongue position sensor 160 illustrated in FIGS. 2-5, and/or the tongue position sensor 180 illustrated in FIGS. 6 and 7) configured to receive signals regarding the position of the tongue 106 (see FIGS. 4 and 5) or the force exerted by the tongue 106 onto the sensor(s) 112. The signal interface 230 may include any standard electrical interface known in the art for connecting a signal carrying wire to a conventional circuit board as well as any components capable of communicating a low voltage time varying signal received from the sensor(s) 112 through an internal bus 240 to the processor(s) 200. The signal interface 230 may include hardware components such as memory as well as standard signal processing components such as an analog to digital converter, amplifiers, filters, and the like.

The control unit 130 may include an electrical stimulation interface 250 connected to the electrode(s) 114 (e.g., the electrode(s) 162 and 164 illustrated in FIGS. 2 and 5, and/or the electrode(s) 182 illustrated in FIG. 7). In wired embodiments, the electrical stimulation interface 250 is configured to deliver electrical stimulation pulses (e.g., charge-balanced pulses) to the electrode(s) 114. In such embodiments, the electrical stimulation interface 250 may include any standard electrical interface known in the art for connecting a signal-carrying wire to a conventional circuit board as well as any components capable of communicating a low voltage time-varying signal generated by the processor(s) 200 or a signal generating device (e.g., like the signal generating device 179 illustrated in FIG. 5) controlled by the processor(s) 200 to the electrode(s) 114 through the internal bus 240. The control unit 130 is configured to generate voltage waveforms that are delivered to the electrode(s) 114 and applied thereby as the stimulation to the hard palate 108 (see FIGS. 4 and 9B). The electrical stimulation interface 250 may include hardware components such as memory as well as standard signal processing components such as a digital to analog converter, amplifiers, filters, and the like. Alternatively, in wireless embodiments, the electrical stimulation interface 250 may include a communication interface configured to communicate commands or instructions from the processor(s) 200 to the intraoral stimulation device(s) 110, which generates the electrical stimulation delivered by the electrode(s) 114 based on the commands or instructions.

The various components of the control unit 130 may be coupled together by the internal buses 240, which may include a single bus or multiple buses connected together and configured to communicate with one another. The internal bus 240 may be constructed using a data bus, control bus, power bus, I/O bus, and the like. The internal bus 240 may be wireless.

The control unit 130 may be fabricated using a combination of computer hardware, an interface board, and custom electronics configured to interface directly or indirectly with the sensor(s) 112 and/or the stimulating electrode(s) 114. For example, the control unit 130 may be fabricated using discrete logic components and/or analog circuit elements.

The control unit 130 may log or store data locally (e.g., in the data 216 stored in the memory 210) and communicate (e.g., upon request) at least a portion of the data 216 to the computing device 120.

The control unit 130 may provide analog to digital ("A/D") conversion as well as digital to analog ("D/A")

conversion. For example, the signal interface 230 may convert analog tongue position information received from the sensor(s) 112 into a digital signal for use by the processor(s) 200. Similarly, the electrical stimulation interface 250 may convert a digital stimulation signal received from the processor(s) 200 into an analog stimulation signal that is delivered to the electrode(s) 114.

Optionally, the control unit 130 may include one or more audible alarms 260.

Optionally, the control unit 130 may be used to calibrate the upper bite block 110U and/or its software, if present.

Referring to FIG. 8, optionally, the control unit 130 may be configured to be attached to a wristband 278 or a headband 280. Together the control unit 130 and the headband 280 may form a headband assembly 282. The headband assembly 282 may be worn on the head 284 of the patient 102 overnight. The headband assembly 282 may be configured to be comfortable to wear as well as easy to wear and clean. The headband assembly 282 may be stable and remain in position overnight. When present, the wiring 169 (see FIGS. 2 and 3) and/or the wiring 184, may be routed to the control unit 130 (see FIGS. 1, 4, 5, and 7) attached to the headband 280, which helps reduce the likelihood of the patient 102 becoming entangled in the wiring 169 and/or the wiring 184 and thereby placing tension on the upper bite block 110U and/or the lower bite block 110L, respectively.

Power Source

Referring to FIG. 1, during operation of a wired embodiment, the power source 132 is not required to provide a lot of power to the control unit 130 and the intraoral stimulation device(s) 110. For example, both the control unit 130 and the intraoral stimulation device(s) 110 may be powered by four 9V transistor batteries providing a total of 2000 milliamp hours. Thus, the power source 132 may be implemented as a typical thin format rechargeable cellphone battery configured to deliver about 2000 mAHr to about 2400 mAHr and may be attached to the headband 280 (see FIG. 8) and form part of the headband assembly 282 (see FIG. 8). By way of another non-limiting example, the power source 132 may be a battery configured to provide ±18 Volts.

Computing System

Figure 10:
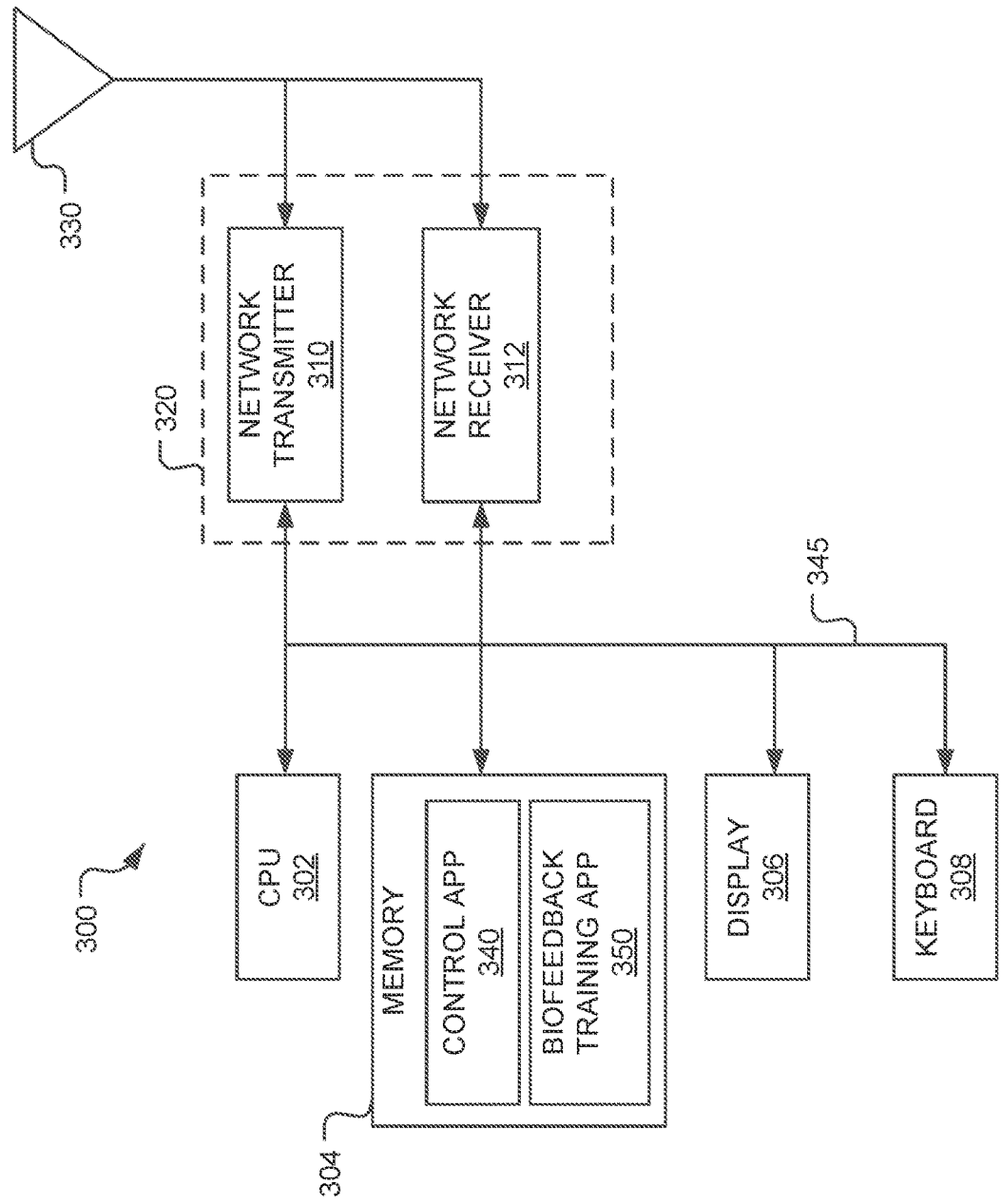
FIG. 10 is a block diagram of an exemplary computing system of FIG. 1.

FIG. 10 is a functional block diagram illustrating a mobile communication device 300 that may be used to implement the computing device 120 (see FIGS. 1 and 8). By way of non-limiting examples, the mobile communication device 300 map be implemented as a laptop computer, a tablet computer, a smartphone, a cellular telephone, any computing device, and the like.

The mobile communication device 300 includes a central processing unit (CPU) 302. Those skilled in the art will appreciate that the CPU 302 may be implemented as a conventional microprocessor, application specific integrated circuit (ASIC), digital signal processor (DSP), programmable gate array (PGA), or the like. The mobile communication device 300 is not limited by the specific form of the CPU 302.

The mobile communication device 300 also contains a memory 304. The memory 304 may store instructions and data to control operation of the CPU 302. The memory 304 may include random access memory, ready-only memory, programmable memory, flash memory, and the like. The memory 304 may include external storage, such as cloud storage. The mobile communication device 300 is not limited by any specific form of hardware used to implement the memory 304. The memory 304 may also be integrally formed in whole or in part with the CPU 302.

The mobile communication device 300 also includes conventional components, such as a display 306 and keyboard or keypad 308. The display 306 may be implemented as a touchscreen user interface. In such embodiments, the keypad 308 may be omitted from the mobile communication device 300. The display 306 and the keypad 308 are conventional components that operate in a known manner and need not be described in greater detail. Other conventional components found in wireless communication devices, such as a USB interface, Bluetooth interface, camera/video device, infrared device, and the like, may also be included in the mobile communication device 300. For the sake of clarity, these conventional elements are not illustrated in the functional block diagram of FIG. 10.

The mobile communication device 300 also includes a network transmitter 310 such as may be used by the mobile communication device 300 for normal network wireless communication with a base station (not shown). FIG. 10 also illustrates a network receiver 312 that operates in conjunction with the network transmitter 310 to communicate with the base station (not shown). In a typical embodiment, the network transmitter 310 and network receiver 312 are implemented as a network transceiver 320. The network transceiver 320 is connected to an antenna 330. Referring to FIG. 1, the antenna 330 (see FIG. 10) is configured to communicate wirelessly with the external device interface 220 over the connection 124. Returning to FIG. 10, operation of the network transceiver 320 and the antenna 330 for communication with a wireless network (not shown) is well-known in the art and need not be described in greater detail herein.

In alternate embodiments, referring to FIG. 1, the connection 124 between the control unit 130 and the computing device 120 may include a wired connection that includes isolation modules (not shown), such as high voltage isolation modules. In such embodiments, the computing device 120 may include a wired interface (not shown) configured to communicate with the control unit 130 over the wired connection.

Referring to FIG. 1, the mobile communication device 300 may also include a conventional geolocation module (not shown) operable to determine the current location of the mobile communication device 300.

The various components illustrated in FIG. 10 are coupled together by a bus system 345. The bus system 345 may include an address bus, data bus, power bus, control bus, and the like. For the sake of convenience, the various busses in FIG. 10 are illustrated as the bus system 345.

The memory 304 may store instructions executable by the CPU 302. Such instructions may be stored on one or more non-transitory computer or processor readable media. The instructions may include a control application 340 and a biofeedback training application 350 stored in the memory 304. The control application 340 and/or the biofeedback training application 350 may be configured to track apnea episodes, log tongue position, and log stimulation profiles. In this manner, the computing device 120 may track disease progression or treatment efficacy over time.

Referring to FIG. 1, while the computing device 120 is illustrated as being a separate component from the control unit 130, in an alternate embodiment, the functionality of the computing device 120 and the control unit 130 may be combined into a single component. This single component may be configured to be attached to the headband 280 (see FIG. 8) and worn on the head of the patient 102 (see FIGS. 4 and 8) overnight.

Control Application

Referring to FIG. 1, the control unit 130 and the intraoral stimulation device(s) 110 may be managed by the control application 340 (see FIG. 10) executing on the computing device 120 (e.g., the mobile communication device 300 illustrated in FIG. 10). The control application 340 (see FIG. 10) provides an interface between a user (e.g., the patient 102 illustrated in FIGS. 4 and 8) and the control unit 130 and/or the intraoral stimulation device(s) 110. The control application 340 may be used to manage the control unit 130 and/or the intraoral stimulation device(s) 110 as well as monitor status of these components. For example, the user may use the computing device 120 to set operating parameters through a touchscreen user interface (e.g., the display 306 illustrated in FIG. 10). By way of non-limiting examples, the control application 340 (see FIG. 10) may upload a preferred stimulation profile (e.g., derived from the biofeedback training), record and log data (tongue position/stimulation events) received from the control unit 130 during use, and activate the audible alarms 260 (see FIG. 1).

Figure 11:
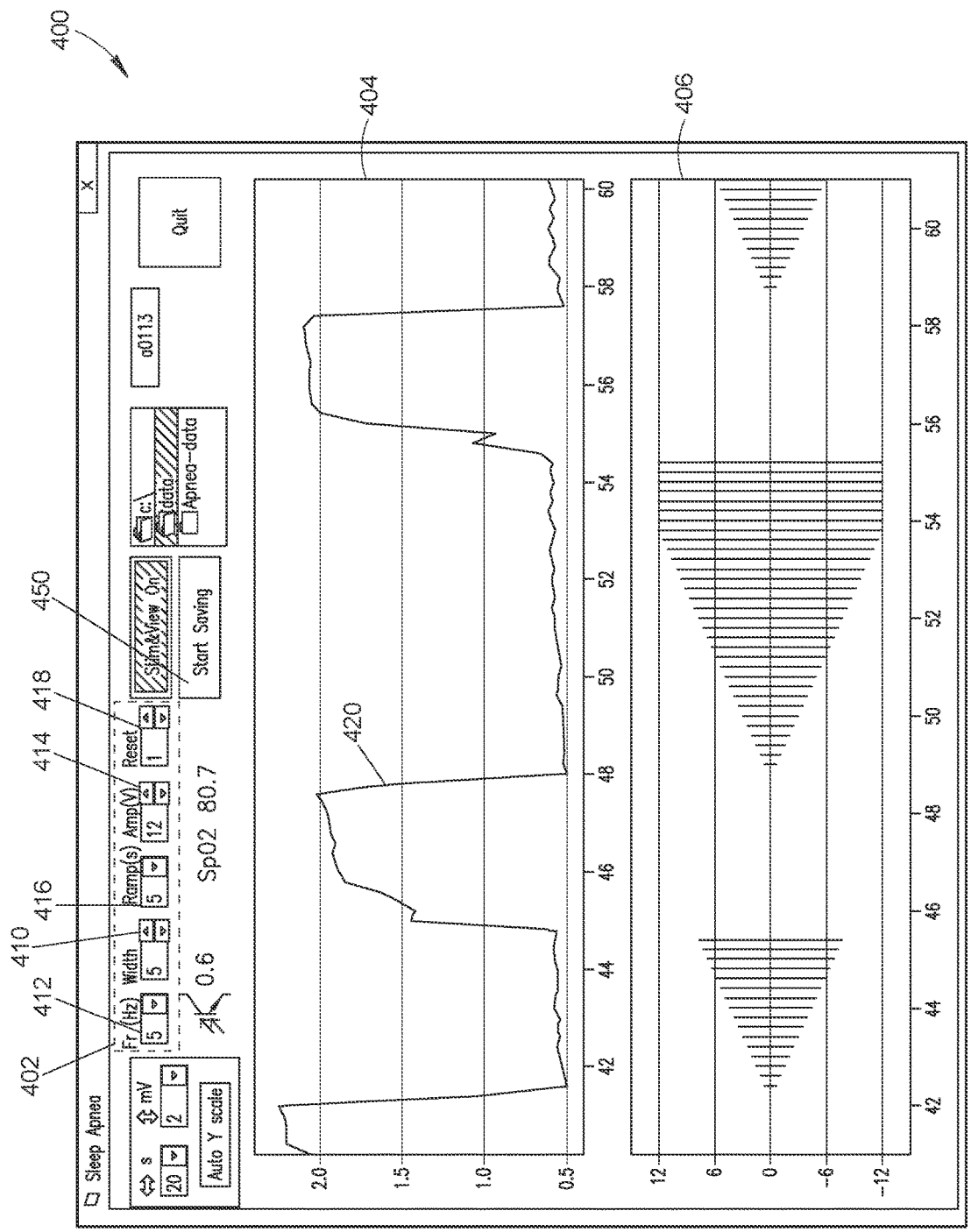
FIG. 11 is an illustration of an exemplary user interface generated by the computing system of FIG. 10.

FIG. 11 illustrates an optional user interface 400 that may be generated by the control application 340 (see FIG. 10). The user interface 400 includes pull-down menus 402 for selecting parameters positioned at or near the top of the user interface 400. The parameters (described below) each have a range from which values can be selected from one of the pull-down menus 402. An upper screen portion 404 shows a signal Sa(V) received from the sensor(s) 112 (see FIG. 1). Progressively higher values indicate extension of the tongue 106 (see FIGS. 4 and 5) towards the sensor(s) 112, the tongue 106 contacting with the sensor(s) 112, and an amount of force exerted by the tongue 106 against the sensor(s) 112. A lower screen portion 406 shows the amplitude of the electrical stimuli that is applied to the integument of the hard palate 108 (see FIGS. 4 and 9B).

When the user interface 400 is first launched (or started), the parameters are assigned initial values (e.g., specified in an initiation file, which may also specify ranges for the two screen portions 404 and 406). A sample initiation file (e.g., named "apnea.ini") is provided below. The initiation file may be implemented as an asci text file and may be customized for a particular patient, in which case, the user does not need to change any of the parameter values after the user interface 400 is started. However, the user can change these parameter values, but in most cases this should not be necessary. The initiation file may be changed by the user using the pull-down menus 402 so when the user interface 400 is re-started, the initial parameter values are those last selected by the user. The parameter values for a particular patient can be restored by copying their personal parameter values (e.g., stored in a personal initiation file) to initiation file.

The following are sample parameters stored by the initiation file (e.g., apnea.ini):

[Setup]
SaveDir=d:\data
FileName=a0131
AOFreq=10
RContact=18
XScale=20
YLimit=20
AO0PIsWidth=5
AO0RampTime=10
AO0MaxAmp=8
AO0ResetAmp=2

The parameters may include a Width parameter, an AOFreq parameter, an Amp(V) parameter, a Ramp(s) parameter, and a Reset parameter. In the example file above, the Width parameter is identified as "AO0PIsWidth" and assigned an initial value of 5, the Amp(V) parameter is identified as "AO0MaxAmp" and assigned an initial value of 8, the Ramp(s) parameter is identified as "AO0RampTime" and assigned an initial value of 10, and the Reset parameter is identified as "AO0ResetAmp" and assigned an initial value of 2.

The Width parameter is the duration (e.g., in msec) of each phase of the biphasic, controlled-voltage stimulus pulses that are applied to the patient's mouth. The pull-down menus 402 include a width menu 410 that may be used to provide the value of the Width parameter. By way of non-limiting examples, the width menu 410 may include the following selectable parameter values: 5 msec per phase, 10 msec per phase, 15 msec per phase, and 20 msec per phase. First and second phases of the electronic stimulation may have opposite polarities and may be automatically set to the same duration. The initial parameter value specified for the Width parameter may be 5 msec per phase. However, this is not a requirement.

The AOFreq parameter is a stimulus pulse rate (e.g., specified in pulses per second ("pps") or hertz) of the controlled-voltage stimulus. The pull-down menus 402 include a AOFreq menu 412 that may be used to provide the value of the AOFreq parameter. By way of non-limiting examples, the AOFreq menu 412 may include the following selectable parameter values: 5 pps, 10 pps, and 20 pps. The initial parameter value specified for the AOFreq parameter may be 10 pps (or 10 Hz). However, this is not a requirement.

The Amp(V) parameter is the maximum amplitude (e.g., in volts) of the stimulus pulses. The pull-down menus 402 include an Amp(V) menu 414 that may be used to provide the value of the Amp(V) parameter. By way of non-limiting examples, the Amp(V) menu 414 may include the following selectable parameter values: 1 V, 2 V, 3 V, 4 V, 5 V, 6 V, 7 V, 8 V, 9 V, 10 V, 11 V, and 12 V. The initial parameter value specified for the Amp(V) parameter may be 8 V. However, this is not a requirement.

The Ramp(s) parameter is the number of seconds required for the electrical stimulus to increase from 0 to the value of the Amp(V) parameter. The pull-down menus 402 include a Ramp(s) menu 416 that may be used to provide the value of the Ramp(s) parameter. By way of non-limiting examples, the Ramp(s) menu 416 may include the following selectable parameter values: 1 sec, 2 sec, 3 sec, 4 sec, 5 sec, 6 sec, 7 sec, 8 sec, 9 sec, 10 sec, 11 sec, 12 sec, 13 sec, 14 sec, 15 sec, 16 sec, 17 sec, 18 sec, 19 sec, and 20 sec. The initial parameter value specified for the Ramp(s) parameter may be seconds. However, this is not a requirement.

The Reset parameter is the amplitude of the signal Sa(V) received from the sensor(s) 112 that causes the stimulus amplitude to reset to 0 volts. The signal Sa(V) is displayed as a continuous trace 420 in the upper screen portion 404 of the user interface 400. The pull-down menus 402 include a Reset menu 418 that may be used to provide the value of the Reset parameter. By way of non-limiting examples, the Reset menu 418 may include selectable parameter values ranging from 1 V to 10 V in steps of 0.1 V. The value of the Reset parameter may be pre-set for each patient. For example, the Amp(V) parameter may be set to a low value (e.g., 2 volts or less), so that the Reset parameter may be adjusted without the patient receiving a perceptible electrical stimulus. Next, the patient 102 (see FIGS. 4 and 8) may place the intraoral stimulation device(s) 110 (see FIGS. 1, 9A, and 9B) into their mouth and the user sets the Reset parameter to 0.1 V below a value indicated by the trace 420 when the patient's tongue 106 (see FIGS. 4 and 5) is extended over the sensor(s) 112 (see FIG. 1). The trace 420 should start to decrease when the patient's tongue retracts from the sensor(s) 112. After the appropriate value of the Reset parameter has been determined, this can be entered into the patient's personal initiation file.

Figure 12:
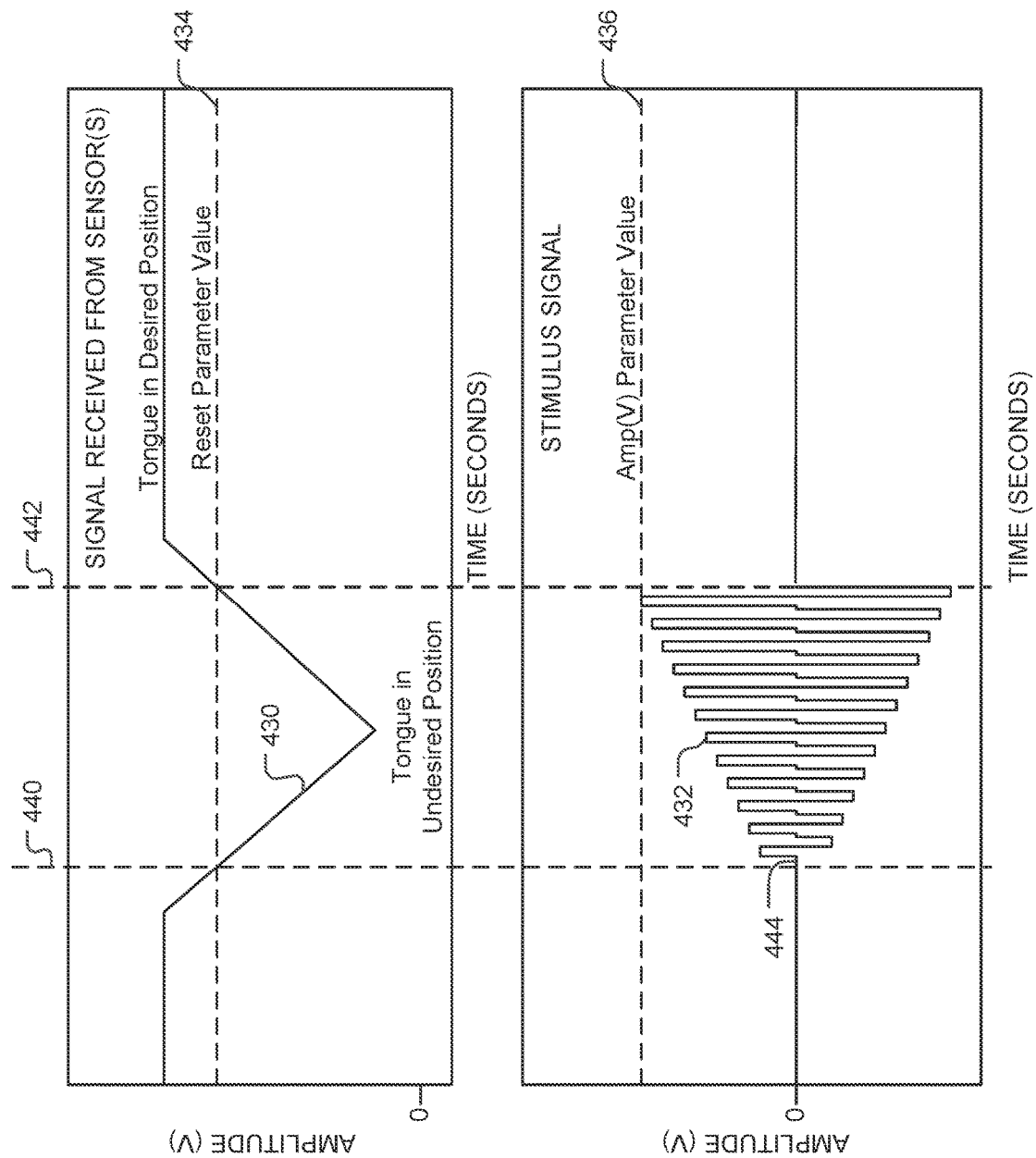
FIG. 12 illustrates traces of a signal received by the control unit from one or more sensors of the intraoral stimulation device(s) and an electrical stimulation sent by the control unit to one or more electrodes of the intraoral stimulation device(s) and delivered to the patient thereby.

FIG. 12 illustrates the control application 340 using the parameter values to deliver stimulus. In FIG. 12, a line 430 illustrates the amplitude of the signal Sa(V) received from the sensor(s) 112 (see FIG. 1) and a line 432 illustrates the amplitude of the stimulation signal delivered by the electrode(s) 114 (see FIGS. 1, 9A, and 9B) to the hard palate 108 (see FIGS. 4 and 9B). In FIG. 12, the stimulation signal is delivered as a series of biphasic pulses. By way of a non-limiting example, the biphasic pulses may have a pulse rate of 5 pulses per second and a duration of each phase may be about 5 milliseconds. The amplitude of the pulses in the series steady increases. The amplitude may return to zero after each biphasic pulse pair, and remain at zero (e.g., for about 190 msec) until the next pulse pair begins A dashed line 434 illustrates the value of the Reset parameter and a dashed line 436 illustrates the value of the Amp(V) parameter. A vertical dashed line 440 illustrates when the line 430 has fallen below the dashed line 434, which means that the amplitude of the signal Sa(V) has fallen below the value of the Reset parameter. A vertical dashed line 442 illustrates when the line 430 has risen above the dashed line 434, which means that the amplitude of the signal Sa(V) is equal to or greater than the value of the Reset parameter.

When the amplitude of the signal Sa(V) (represented by the line 430) falls below the value of the Reset parameter (represented by the dashed line 434), indicating that the tongue 106 (see FIGS. 4 and 5) is retracting from the sensor(s) 112 (see FIG. 1), the pulsatile stimulation is applied to mucosal lining of the hard palate 108 (see FIGS. 4 and 9B) through the electrode(s) 114 (see FIGS. 1, 9A, and 9B). The ramp-up of the stimulus amplitude from zero volts toward the value of the Amp(V) parameter (represented by the dashed line 436) may begin after a delay 444 (e.g., 1 second) that may be hard-coded in the control application 340 (see FIG. 10). Initially, the stimulus amplitude (represented by the line 432) is zero volts, but increases to the value of the Amp(V) parameter (represented by the dashed line 436), where it remains until the patient 102 moves their tongue 106 forward and causes the amplitude of the signal Sa(V) to fall below the value of the Reset parameter, whereupon the stimulus amplitude is immediately reset to zero volts. As mentioned above, the stimulus amplitude may increase over the predetermined time period (e.g., about 5 seconds to about 7 seconds).

The value of the Reset parameter may greater than the amplitude of the signal Sa(V) (represented by the line 430) when the tongue 106 just contacts the sensor(s) 112, so that the tongue 106 must exert at least a prescribed amount of force against the sensor(s) 112, thereby increasing the tone in the tongue extensor muscles above what would be required to simply contact the sensor(s) 112.

The control application 340 (see FIG. 10) continuously records (e.g., at interval of about one second) the output (represented by the line 430) of the sensor(s) 112, and the voltage of the amplitude (represented by the line 432) of the electrical stimulus (e.g., delivered in pulses). By way of a non-limiting example, this data saving may be initiated by the user selecting a START SAVING option 450. By way of a non-limiting example, the data may be saved in Microsoft Excel ("xl") format. The control application 340 (see FIG. 10) may also record the patient's hemoglobin saturation, as monitored by a finger clip pulse oximeter.

Biofeedback Training Application

Referring to FIG. 4, maintaining the tongue 106 in a desired (forward) position requires that the patient 102 maintain a small tone in the tongue extensor muscles. This behavior may be induced in the patient 102 and maintained by induction of a new reflex (or conditioned response), using biofeedback to induce and maintain the reflex. Prior investigators who have researched treating obstructive sleep apnea have not considered biofeedback-based training systems that function to generate and/or reinforce a conditioned reflex whereby the tongue 106 is moved forward and into contact with the lower incisors in response to weak electrical stimulation delivered to the surface of the anterior hard palate 108. Referring to FIG. 10, the biofeedback training application 350 implements such biofeedback-based training.

The biofeedback training application 350 may upgrade and/or program the control application 340 depending on data collected from the sensor(s) 112 (see FIG. 1) and action of the stimulating electrode(s) 114 (see FIGS. 1, 9A, and 9B). As the patient's tongue 106 (see FIGS. 4 and 5) becomes trained to move forward in response to weak electrical stimulation, it is expected that lower stimulus voltages will be required. Data collected from the sensor(s) 112 may be used to calibrate the control unit 130 and/or its software (e.g., the instructions 214 illustrated in FIG. 1).

The user (e.g., the patient 102 illustrated in FIGS. 4 and 8) may use a touchscreen user interface (e.g., the display 306 illustrated in FIG. 10) of the computing device 120 (see FIGS. 1 and 8) to implement the biofeedback training. Referring to FIG. 10, the biofeedback training application 350 may be gamified to improve training and engage the user (e.g., the patient 102) in the training process. The biofeedback training application 350 provides an interface between the user and the control unit 130 and the intraoral stimulation device(s) 110. This interface provides visual feedback regarding both tongue position and stimulation that is used to implement a training protocol (and later for airway rehabilitation training).

Biofeedback based training is based at least in part on conditioned responses and conditioned protective/avoidance reflexes. The phenomenon of conditioned (or conditional) reflexes first was investigated systematically by the Russian physician and physiologist Ivan Pavlov (1874-1936). Behavior that is not innate can be "conditioned" and thus becomes automatic and "unconscious" by repeated pairing of a conditioned stimulus with a (non-conditioned) stimulus to which the behavior is innately linked. A related phenomenon is the conditioned protective reflex, in which an individual becomes conditioned to automatically initiate an action that will preclude pain or injury in response to a non-injurious, non-noxious percept that is paired with the onset of the noxious stimulus.

For example, referring to FIG. 4, the patient 102 will reflexive withdraw the tongue 106 from between the patient's incisors upon perception of dental pressure against the tongue 106. This occurs because the patient 102 has been conditioned to associate the percept of moderate (bite) pressure against the tongue 106 with the probability of subsequent pain and injury to the tongue 106, unless an appropriate protective response is initiated (e.g., withdrawal of the tongue 106 from between the incisors).

The biofeedback training application 350 (see FIG. 10) may be used to provide biofeedback based training that trains the patient 102 to position the patient's tongue 106 such that the patient's tongue 106 does not obstruct the patient's UA 104. The upper bite block 110U and/or the lower bite block 110L (see FIGS. 6 and 7) may be used to perform a biofeedback-based method, which may generate (or induce) and maintain, in the patient 102, a conditioned reflex whereby the tongue 106 is moved anteriorly and/or dorsally in response to very weak electrical stimulation delivered to the hard palate 108. In other words, the conditioned reflex means lower amplitude stimulation is needed to induce the tongue 106 to move from an undesired to a desired position. The biofeedback-based mode may be used alone or in combination with a mode wherein the movement of the tongue 106 is produced directly by electrical stimulation applied through the (sublingual) electrode(s) 182 (see FIG. 7) to branches of the hypoglossal nerve. The biofeedback training application 350 (see FIG. 10) may apply the conditioning electrical stimulus through the electrode(s) 114 (see FIG. 1) that contact the hard palate 108, and/or through the (sublingual) electrode(s) 182 (see FIG. 7). The (sublingual) electrode(s) 182 (see FIG. 7) may also directly stimulate the nerves that extend the tongue 106.

Figure 13:
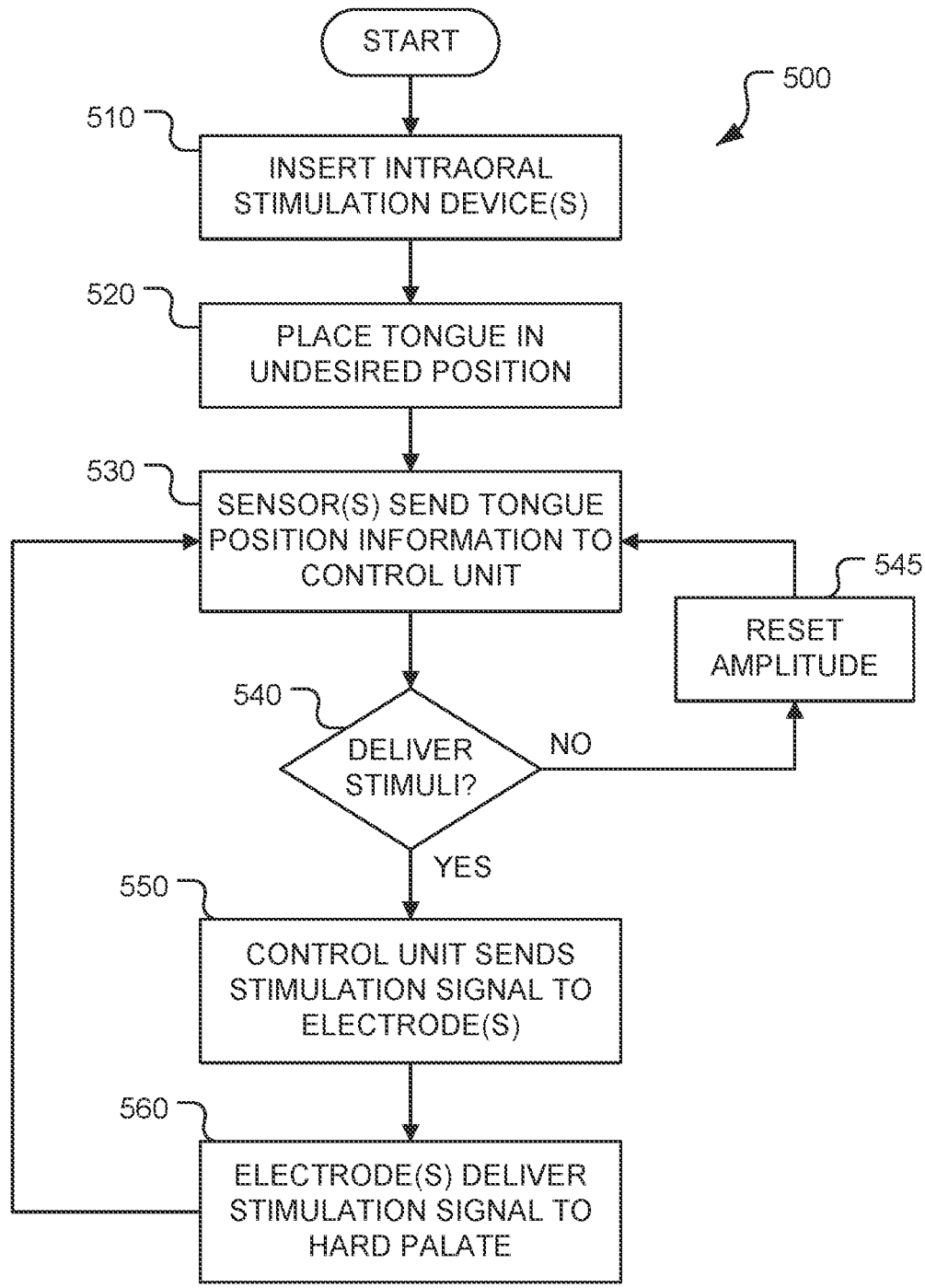
FIG. 13 is a flow diagram of a method that may be performed by the system of FIG. 1.

Referring to FIG. 1, the biofeedback training application 350 (see Figure implements a training phase during which the patient 102 (see FIGS. 4 and 8) is trained to have the conditioned response (or reflex) in response to the electrical stimuli delivered by the electrode(s) 114. During the training phase, the patient 102 experiences a number of substantially identical sessions. FIG. 13 is a flow diagram of a method 500 that may be performed during a session of the training phase. In first block 510, the patient 102 inserts the intraoral stimulation device(s) 110. Then, in block 520, while awake, the patient 102 places the patient's tongue 106 in an undesired position (e.g., retracted from the sensor(s) 112). At this point, the stimulation parameters are assigned their initial values (discussed above) by the control unit 130, which are configured to deliver weak electrical stimulation. In block 530, the sensor(s) 112 send signal(s) encoding tongue position information to the control unit 130.

In decision block 540, the control unit 130 determines whether to send the stimulation signal to the electrode(s) 114 based on the tongue position information. The decision in decision block 540 is "YES" when the control unit 130 determines that the patient's tongue 106 is in the undesired position. Otherwise, the decision in decision block 540 is "NO." When the decision in decision block 540 is "NO," in block 545, the control unit 130 resets the amplitude of the stimulation back to its initial value. Then, the method 500 returns to block 530.

On the other hand, when the decision in decision block 540 is "YES," in block 550, the control unit 130 configures the electrical stimulation and sends it to the stimulating electrode(s) 114. In block 560, the stimulating electrode(s) 114 deliver the electrical stimulation to the hard palate 108. Then, the method 500 returns to block 530.

The first time the block 550 is performed, the electrical stimulation configured by the control unit 130 is based on the initial stimulation parameter values. Thus, the electrical stimulation is relatively weak, having a low amplitude that is barely perceptible to the patient 102. Each successive time block 550 is performed without the amplitude being reset in block 545, the control unit 130 increases the amplitude of the electrical stimulation until the tongue 106 moves to the desired position (e.g., touching or pressing upon the tongue position sensor 160 and/or the tongue position sensor 180), which results in the decision in decision block 540 being "NO." In some cases, the electrical stimulation may become uncomfortable to the patient 102, which will encourage the patient 102 to develop the conditioned reflex.

After the training phase is complete, the patient 102 has acquired the conditioned response (or reflex). Thus, the method 500 may be used to treat OSA when the patient 102 is asleep. In such embodiments, the block 520 is omitted after block 510. In block 530, the sensor(s) 112 send signal(s) encoding tongue position information to the control unit 130. When the control unit 130 determines the patient's tongue 106 in an undesired position in decision block 540, the tongue 106 may be moved to the desired position by electrical stimulation delivered to the hard palate 108 by the stimulating electrode(s) 114 (in blocks 550 and 560). As occurred during each of the sessions, the electrical stimulation delivered to the sleeping patient 102 may start out as weak electrical stimulation. If the tongue 106 does not move to the desired position in response to the weak electrical stimulation, the control unit 130 may continuously increase the amplitude of the electrical stimulation until the tongue 106 moves to the desired position.

Maintaining the tongue 106 in a desired (forward) position requires that the patient 102 maintain a small tone in the tongue extensor muscles. This behavior by the patient 102 may be induced and maintained by induction of this new reflex (or conditioned response), using biofeedback to induce and maintain the reflex.

Figure 14:
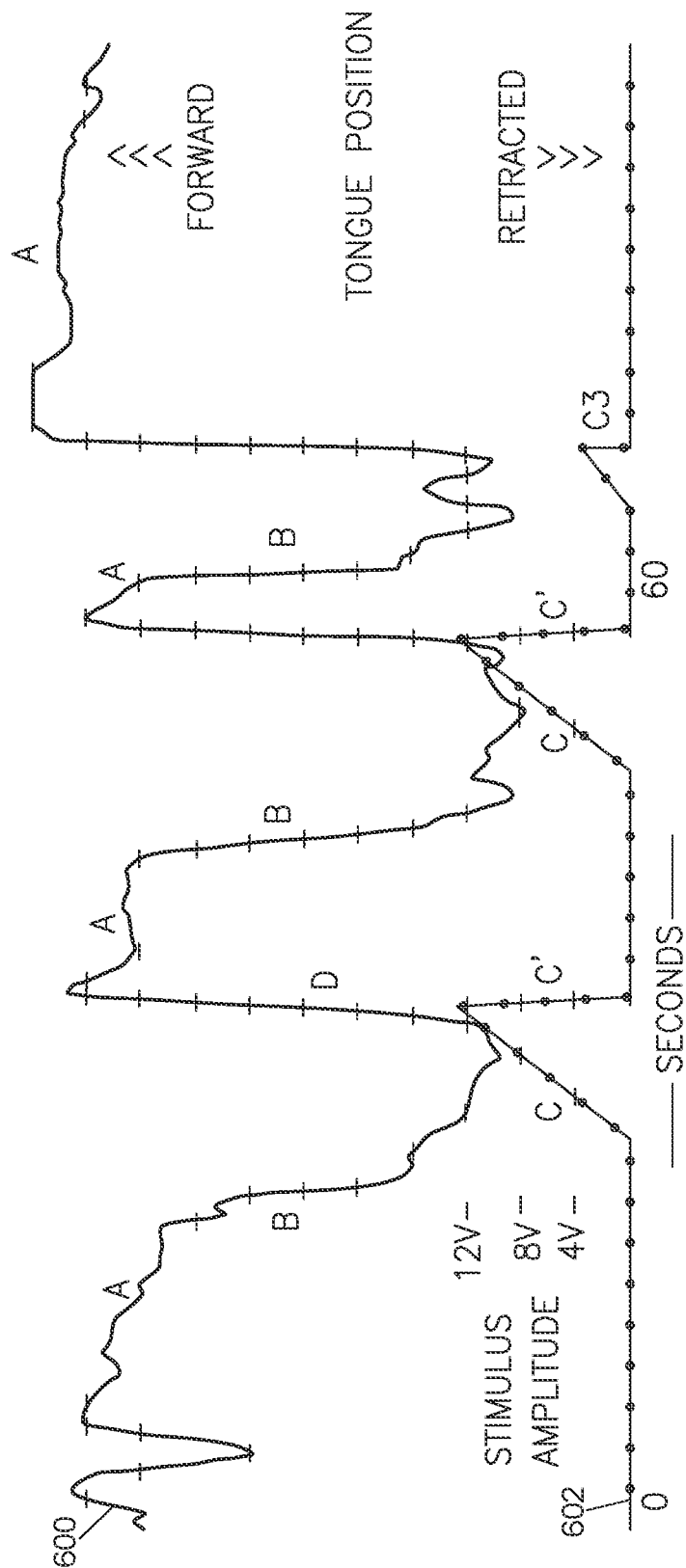
FIG. 14 illustrates traces of a signal received by the control unit from one or more sensors of the intraoral stimulation device(s) and an electrical stimulation sent by the control unit to one or more electrodes of the intraoral stimulation device(s) and delivered to the patient thereby.

FIG. 14 is a graph showing a 90-second snippet of data captured from the upper bite block 110U (see FIGS. 2-5) during use in the patient's mouth during sleep. In FIG. 14, a line 600 illustrates the amplitude of the signal Sa(V), which represents tongue position as determined by the tongue position sensor 160 (see FIGS. 2-5). A line 602 illustrates the amplitude of the electrical stimulation delivered to the patient's hard palate 108 (see FIGS. 4 and 9B). FIG. 14 illustrates the position of the tongue 106 (represented by the line 600) of the patient 102 (see FIGS. 4 and 8) who has developed a tongue extension reflex in response to the sessions of stimulation of the hard palate 108 with the graded stimulus while awake. The letters A-D in FIG. 14 correspond to the following:

A. The tongue 106 (see FIGS. 4 and 5) moves forward in patient's mouth, close to the tongue position sensor 160
B. The tongue 106 retracting from the tongue position sensor 160;
C. Electrical stimulus to patient's hard palate 108 (see FIGS. 4 and 9B) begins, in response to retracting of the tongue 106; amplitude of stimulus increases continuously during the next 15 seconds, until the tongue 106 moves forward; and
D. Patient's tongue 106 moves forward and electrical stimulus to the hard palate 108 stops (represented by line segments "C").

As shown in FIG. 14, the electrical stimulus (represented by the line 602) begins (represented by line segments "C") when the tongue 106 is retracted from the tongue position sensor 160 (see FIGS. 2-5). As shown by the line portions "C," the amplitude of the electrical stimulus increased continuously while the tongue 106 (see FIGS. 4 and 5) remained retracted from the tongue position sensor 160. As shown by the line portions "C," the electrical stimulus ceases when the tongue 106 moved forward.

The method 500 may be characterized as being a biofeedback-based method, in which an invariant sequence of events is performed. Referring to FIG. 13, when the control unit 130 first detects the tongue 106 is retracted from the tongue position sensor 160 and the decision in decision block 540 is "YES," in block 550, the control unit 130 initiates an onset of low-amplitude stimulation that is barely perceptible to the patient 102. This stimulation is delivered by the electrode(s) 114 (see FIGS. 1, 9A, and 9B) in block 560. Then, if the control unit 130 again detects that the tongue 106 is retracted from the tongue position sensor 160 and the decision in decision block 540 is "YES," in block 550, the control unit 130 increases the amplitude of the stimulus sent to the electrode(s) 114 (see FIGS. 1, 9A, and 9B), which is delivered thereby in block 560. As long as the control unit 130 continues to detect that the tongue 106 is retracted from the tongue position sensor 160, the control unit 130 continuously increases the amplitude of the stimulation, which may become uncomfortable to the patient 102 (see FIGS. 4 and 8).

In other words, initially, the amplitude of the stimulus pulses is very low and imperceptible to the patient 102, but if the tongue 106 (see FIGS. 4 and 5) remains retracted from the tongue position sensor 160 (e.g., in a posterior position) or if the tongue 106 does not exert the prescribed force upon the tongue position sensor 160, the stimulus amplitude increases steadily (e.g., over an interval of 10 seconds to 20 seconds) becoming perceptible as a tactile sensation, and, if continued, becoming mildly uncomfortable as the stimulus amplitude increases and delivers strong (or high-amplitude) stimulation to the hard palate 108.

Finally, when the control unit 130 detects the tongue 106 is in the desired position and the decision in decision block 540 is "NO," meaning no stimulation is delivered. Thus, the stimulation immediately terminates when the tongue 106 (FIG. 6) moves anteriorly and into contact with the tongue position sensor 160.

The patient 102 (see FIGS. 4 and 8) must experience the above sequence of events many times, first while awake, for the repositioning of the tongue 106 (see FIGS. 4 and 5) to become automatic, or "conditioned," so that the tongue 106 move will move forward in response to the onset of barely perceptible low-level (e.g., low amplitude) stimulation. This training of the conditioned response may first be administered when the subject is awake, but later it may be maintained and reinforced when the subject is asleep by the action of the control unit 130 (see FIGS. 1, 4, 5, and 7). The control unit 130 continues to administer the sequence of events described above whenever the patient's tongue 106 retracts from the tongue position sensor 160.

As shown in FIG. 14, at line segment C3, the patient's tongue 106 moved forward as soon as the stimulus began and remained forward near the tongue position sensor 160, which indicates that training has taken place and the conditioned reflex has been acquired by the patient 102.

The conditioned reflex persists during sleep in response to a level of electrical stimulation that will not disturb sleep. Thus, this conditioned reflex is like other acquired protective and/or defensive oral reflexes, including opening of the jaw and retraction of the tongue 106 (see FIGS. 4 and 5) in response to light (but non-painful) bite pressure against the tongue 106. The amplitude and pulse rate of the electrical stimulus can be adjusted (e.g., using the control application 340) so that the most intense electrical stimulation experienced by the patient 102 will be an unpleasant "prickling" sensation.

In FIG. 14, the electrical stimulus applied to the patient's hard palate 108 (see FIGS. 4 and 9B) was a train of biphasic voltage pulses. As discussed above, the phase duration, pulse rate, and maximum amplitude (voltage) may be set by the user using the user interface 400 (see FIG. 11). In FIG. 14, the pulse rate was 5 pulses per second and duration of each phase was 5 milliseconds. The line 602 shows the amplitude of each 5 msec pulse, as the pulse amplitude steady increases. In actuality, the stimulus amplitude returned to 0 V after each biphasic pulse pair, and remained at 0 V for about 190 msec, until the next pulse pair began.

Referring to FIG. 1, the control unit 130 may decide to deliver stimulation in decision block 540 (see FIG. 13) when the sensor(s) 112 detect that the tongue 106 (see FIGS. 4 and 5) is not in an anterior position and particularly in its most anterior position. Alternatively, the control unit 130 may be adjusted to begin the electrical stimulation whenever the tongue 106 (see FIGS. 4 and 5) is not exerting a prescribed amount of force upon the sensor(s) 112 (e.g., the tongue position sensor 160 illustrated in FIGS. 2-5). For example, referring to FIG. 4, the prescribed amount of force against the tongue position sensor 160 needed to terminate stimulation may be about zero grams to about 150 grams. The lower force value (zero grams) allows the tongue's position alone (i.e., merely contacting the tongue position sensor 160) to terminate stimulation, which in some patients may be adequate to maintain an open airway. In other embodiments, the prescribed amount of force required to terminate stimulation may be about 20 grams to about 100 grams. Such embodiments, the method 500 may be performed when it is determined that additional muscle tone in the muscles of the tongue 106 is required to prevent obstruction of the UA 104.

In various embodiments, the voltage amplitude of the electrical stimulation may be about 5 volts to about 15 volts and the rate may be about 3 pulses per second to about 50 pulses per second. In other embodiments, the voltage amplitude of the electrical stimulation may be about 10 volts to about 25 volts and the rate may be about 5 pulses per second to about 50 pulses per second. It is expected that this will encourage (reinforce) development of a protective reflex whereupon the tongue 106 (see FIGS. 4 and 5) is moved into contact with the sensor(s) 112 and/or exerts a prescribed force upon the sensor(s) 112 in response to the onset of the electrical stimulus, when the amplitude of the electrical stimulus is very low. The movement of the tongue 106 (see FIGS. 4 and 5) may be effected by the acquired or conditioned reflex that is initiated by direct electrical stimulation applied to the hard palate 108, direct electrical stimulation of the motor nerve that extends the tongue 106, or a combination thereof. The stimulus amplitude remains below the charge density that can cause tissue injury. When the tongue 106 is moved anteriorly and makes contact with the sensor (s) 112 or exerts a prescribed force against the sensor(s) 112, the electrical stimulation may cease.

As described above, referring to FIG. 2, the upper bite block 110U (e.g., an individually-fitted maxillary dental fixture or night guard) may maintain extension of the tongue 106 by a conditioned reflex, rather than by direct stimulation of the innervation to the tongue extensor muscles. The upper bite block 110U positions the stimulating electrodes 162 and 164 (see FIGS. 2 and 5) in contact with the stable integument surface of the hard palate 108. The tongue position sensor 160 senses when to deliver the directed stimulation (via the stimulating electrodes 162 and 164). Referring to FIG. 7, the lower bite block 110L may be used in combination with the upper bite block 110U (see FIGS. 2-5) for mouth breathers. Furthermore, training provided by the biofeedback training application 350 is designed so that it is likely that many patients will eventually require less electrical stimulation and some patients may be able to retrain so that use of the upper and/or lower bite blocks 110U and 110L is not required on a regular basis or perhaps, at all.

Referring to FIG. 1, the system 100 may offer advantages over currently available therapies for treating OSA. For example, the system 100 does not include a mask placed on the face of the patient 102 (see FIGS. 4 and 8). The system 100 does not disrupt the position of the patient's temporomandibular joint. The system 100 does not require surgery and the patient's body position during sleep is flexible. Additionally, the patient 102 is not tethered to a hose. Therefore, the patient 102 may be more willing to use the system 100. Thus, the system 100 may have much higher compliance than CPAP or even MDA. The intraoral stimulation device(s) 110 may be configured to fit easily into one or more small cases for traveling. For example, referring to FIG. 8, the upper bite block 110U may be stored in a first case 194 and the lower bite block 110L may be stored in a second case 196.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Conjunctive language, such as phrases of the form "at least one of A, B, and C," or "at least one of A, B and C," (i.e., the same phrase with or without the Oxford comma) unless specifically stated otherwise or otherwise clearly contradicted by context, is otherwise understood with the context as used in general to present that an item, term, etc., may be either A or B or C, any nonempty subset of the set of A and B and C, or any set not contradicted by context or otherwise excluded that contains at least one A, at least one B, or at least one C. For instance, in the illustrative example of a set having three members, the conjunctive phrases "at least one of A, B, and C" and "at least one of A, B and C" refer to any of the following sets: {A}, {B}, {C}, {A, B}, {A, C}, {B, C}, {A, B, C}, and, if not contradicted explicitly or by context, any set having {A}, {B}, and/or {C} as a subset (e.g., sets with multiple "A"). Thus, such conjunctive language is not generally intended to imply that certain embodiments require at least one of A, at least one of B, and at least one of C each to be present. Similarly, phrases such as "at least one of A, B, or C" and "at least one of A, B or C" refer to the same as "at least one of A, B, and C" and "at least one of A, B and C" refer to any of the following sets: {A}, {B}, {C}, {A, B}, {A, C}, {B, C}, {A, B, C}, unless differing meaning is explicitly stated or clear from context.

Accordingly, the invention is not limited except as by the appended claims.

The invention claimed is:

1. A system for treating obstructive sleep apnea in an individual, comprising:
   an intraoral stimulation device, comprising:
      a first dental mouthpiece configured to be positioned on upper teeth of an individual:
      a first sensor mounted on the first dental mouthpiece and configured to monitor at least one of a position of tongue of the individual and force exerted by the tongue of the individual against the first sensor;
      a first electrode mounted on the first dental mouthpiece and configured to deliver an electrical stimulus to an anterior hard palate of the individual; and
   a controller in communication with the intraoral stimulation device and configured to receive a signal from the first sensor indicating a position of the tongue and direct the first electrode to deliver an electrical stimulus, when the first sensor indicates that the tongue has moved from a desired position to an undesired position in the mouth.

2. The system of claim 1, wherein the first electrode is attached to the first dental mouthpiece by a pivot member configured to position the first electrode into contact with the hard palate.

3. The system of claim 1, wherein the intraoral stimulation device further comprises:
   a second dental mouthpiece configured to be positioned on lower teeth of the individual; and
   a second sensor mounted on the second dental mouthpiece and configured to monitor at least one of a position of tongue of the individual and force exerted by the tongue of the individual against the second sensor;
   wherein the controller is further configured to receive a signal from the second sensor; and wherein the controller is configured to direct the first electrode to deliver an electrical stimulus, when the first sensor and the second sensor indicate that the tongue has moved from a desired position to an undesired position in the mouth.

4. The system of claim 3, wherein the intraoral stimulation device further comprises a second electrode mounted on the second dental mouthpiece and configured to deliver an electrical stimulus sublingually to the individual, and wherein the controller is configured to direct the first electrode or the second electrode to deliver an electrical stimulus, when the first sensor and the second sensor indicate that the tongue has moved from a desired position to an undesired position in the mouth.

5. The system of claim 1, wherein the controller is external of the intraoral stimulation device and the intraoral stimulation device further comprises a transponder in electrical communication with the first electrode and the first sensor, wherein the transponder wirelessly communicates with the controller.

6. The system of claim 1, further comprising wiring and a power source, wherein the controller is external of the intraoral stimulation device and the wiring provides the communication between the controller and the intraoral stimulation device and connects the power source to the controller and the intraoral stimulation device.

7. The system of claim 1, wherein the first electrode is capable of providing an increasing amplitude of the electrical stimulus.

8. The system of claim 7, wherein the controller is configured to direct the first electrode to provide an increasing amplitude of the electrical stimulus.

9. The system of claim 7, wherein the controller is configured to direct the first electrode to:
deliver a low-amplitude electrical stimulation;
increase an amplitude of the low-amplitude electrical stimulation to create high-amplitude electrical stimulation, and
deliver the high-amplitude electrical stimulation until the tongue moves from the undesired position to the desired position.

10. The system of claim 1, wherein the controller is further configured to direct the first electrode to terminate the electrical stimulus when the first sensor indicates the tongue has moved from an undesired position to a desired position in the mouth.

11. The system of claim 10, wherein the controller comprises:
a processor; and
a memory containing instructions that when executed by the processor direct the processor to:
receive a signal from the first sensor indicating a position of the tongue;
direct the first electrode to deliver an electrical stimulus, when the first sensor indicates that the tongue has moved from a desired position to an undesired position in the mouth; and
direct the first electrode to terminate the electrical stimulus, when the first sensor indicates the tongue has moved from an undesired position to a desired position in the mouth.

12. The system of claim 1, wherein the controller comprises:
a processor; and
a memory containing instructions that when executed by the processor direct the processor to:
receive a signal from the first sensor indicating a position of the tongue; and
direct the first electrode to deliver an electrical stimulus, when the first sensor indicates that the tongue has moved from a desired position to an undesired position in the mouth.

13. The system of claim 12, wherein the memory further contains instructions that when executed by the processor direct the processor to log data from one or both of the first sensor and the first electrode.

14. The system of claim 13, wherein the data comprises at least one of tongue position as a function of time and electrical stimulus as a function of time.

15. The system of claim 14, wherein the memory further contains instructions that when executed by the processor direct the processor to update electrical stimulation parameters based on a response time for the tongue to move from an undesired position to a desired position in the mouth.

16. The system of claim 12, wherein the memory further contains instructions to implement implements a biofeedback method that adjusts the delivery of the electrical stimulus based on changes over time in at least one of the position of the tongue and the force exerted by the tongue.

17. The system of claim 1, wherein the first sensor comprises an infrared emitter and an infrared detector.

18. The system of claim 17, wherein the infrared emitter and the infrared detector are separated by an opaque partition.

19. The system of claim 1, wherein the controller is integrated within the intraoral device.

20. A system for treating obstructive sleep apnea in an individual, comprising:
an intraoral stimulation device, comprising:
a first dental mouthpiece configured to be positioned on teeth of an individual:
a first sensor mounted on the first dental mouthpiece and configured to monitor at least one of a position of tongue of the individual and force exerted by the tongue of the individual against the first sensor;
a first electrode mounted on the first dental mouthpiece and configured to deliver an electrical stimulus to a mouth of the individual; and
a controller in communication with the intraoral stimulation device and configured to receive a signal from the first sensor indicating a position of the tongue and direct the first electrode to deliver an electrical stimulus, when the first sensor indicates that the tongue has moved from a desired position to an undesired position in the mouth, wherein the controller is external of the intraoral stimulation device and the intraoral stimulation device further comprises a transponder in electrical communication with the first electrode and the first sensor, wherein the transponder wirelessly communicates with the controller.

21. A system for treating obstructive sleep apnea in an individual, comprising:
an intraoral stimulation device, comprising:
a first dental mouthpiece configured to be positioned on teeth of an individual:
a first sensor mounted on the first dental mouthpiece and configured to monitor at least one of a position of tongue of the individual and force exerted by the tongue of the individual against the first sensor;
a first electrode mounted on the first dental mouthpiece and configured to deliver an electrical stimulus to a mouth of the individual; and a controller in communication with the intraoral stimulation device and configured to receive a signal from the first sensor indicating a position of the tongue and direct the first electrode to deliver an electrical stimulus, when the first sensor indicates that the tongue has moved from a desired position to an undesired position in the mouth, wherein the controller comprises:

a processor; and a memory containing instructions that when executed by the processor direct the processor to:

receive a signal from the first sensor indicating a position of the tongue;

direct the first electrode to deliver an electrical stimulus, when the first sensor indicates that the tongue has moved from a desired position to an undesired position in the mouth; and log data from one or both of the first sensor and the first electrode.

22. The system of claim 21, wherein the data comprises at least one of tongue position as a function of time and electrical stimulus as a function of time.

23. The system of claim 22, wherein the memory further contains instructions that when executed by the processor direct the processor to update electrical stimulation parameters based on a response time for the tongue to move from an undesired position to a desired position in the mouth.

24. The system of claim 21, wherein the first dental mouthpiece is configured to be positioned on one or both of upper teeth and lower teeth of the individual.

\* \* \* \* \*